United States Patent
Cao et al.

(10) Patent No.: US 11,155,617 B2
(45) Date of Patent: Oct. 26, 2021

(54) LAG-3 ANTIBODY, ANTIGEN-BINDING FRAGMENT THEREOF, AND PHARMACEUTICAL APPLICATION THEREOF

(71) Applicants: Jiangsu Hengrui Medicine Co., Ltd., Jiangsu (CN); Shanghai Hengrui Pharmaceutical Co., Ltd., Shanghai (CN)

(72) Inventors: Zhuoxiao Cao, Shanghai (CN); Yayuan Fu, Shanghai (CN); Qiyue Hu, Shanghai (CN); Weikang Tao, Shanghai (CN); Lianshan Zhang, Shanghai (CN); Piaoyang Sun, Jiangsu (CN)

(73) Assignees: Jiangsu Hengrui Medicine Co., Ltd., Jiangsu (CN); Shanghai Hengrui Pharmaceutical Co., Ltd., Shanghai (CN)

( * ) Notice: Subject to any disclaimer, the term of this patent is extended or adjusted under 35 U.S.C. 154(b) by 208 days.

(21) Appl. No.: 16/312,174

(22) PCT Filed: Jun. 22, 2017

(86) PCT No.: PCT/CN2017/089492
§ 371 (c)(1),
(2) Date: Dec. 20, 2018

(87) PCT Pub. No.: WO2017/219995
PCT Pub. Date: Dec. 28, 2017

(65) Prior Publication Data
US 2019/0233513 A1 Aug. 1, 2019

(30) Foreign Application Priority Data
Jun. 23, 2016 (CN) .......................... 201610465386.2

(51) Int. Cl.
| | | |
|---|---|---|
| *C07K 16/00* | (2006.01) | |
| *C07K 16/28* | (2006.01) | |
| *A61K 39/395* | (2006.01) | |
| *A61K 39/00* | (2006.01) | |
| *A61P 35/00* | (2006.01) | |

(52) U.S. Cl.
CPC .......... *C07K 16/2803* (2013.01); *A61K 39/00* (2013.01); *A61K 39/395* (2013.01); *A61P 35/00* (2018.01); *C07K 16/28* (2013.01); *C07K 2317/24* (2013.01); *C07K 2317/51* (2013.01); *C07K 2317/565* (2013.01); *C07K 2317/567* (2013.01)

(58) Field of Classification Search
CPC ............... C07K 16/2803; C07K 16/28; C07K 2317/24; C07K 2317/51; C07K 2317/565; C07K 2317/567; A61P 35/00
See application file for complete search history.

(56) References Cited

U.S. PATENT DOCUMENTS

| | | | |
|---|---|---|---|
| 5,976,877 A | 11/1999 | Hercend et al. | |
| 2006/0240024 A1* | 10/2006 | Pardoll | .................. A61P 31/18 424/155.1 |
| 2011/0070238 A1* | 3/2011 | Triebel | ............... C07K 16/2803 424/141.1 |

FOREIGN PATENT DOCUMENTS

| | | |
|---|---|---|
| CN | 101720227 | 6/2010 |
| CN | 102176921 | 9/2011 |
| CN | 102884085 | 1/2013 |
| CN | 105209494 | 12/2015 |
| EP | 519866 A1 * | 12/1992 |
| GB | 2451014 | 12/2010 |
| RU | 2551235 | 5/2015 |
| WO | WO199530750 | 11/1995 |
| WO | WO2004078928 | 9/2004 |
| WO | WO2008055206 | 5/2008 |
| WO | WO2008132601 | 11/2008 |
| WO | WO2010019570 | 2/2010 |
| WO | WO2014008218 | 1/2014 |
| WO | WO2014140480 | 9/2014 |
| WO | WO2014144865 | 9/2014 |
| WO | WO2015042246 | 3/2015 |
| WO | WO2015138920 | 9/2015 |
| WO | WO2016028672 | 2/2016 |

OTHER PUBLICATIONS

Chen et al E. Exp. Med, 176: 855-866, 1992 (Year: 1992).*
Chen et al..,"Enhancement and destruction of antibody function by somatic mutation: unequal occurrence is controlled by V gene combinatorial associations," The EMBO J., 1995, 14(12):2784-2794.
Pakula et al., "Genetic analysis of protein stability and function," Annu. Rev. Genet., 1989, 23:289-310.
Roitt. et al., "Immunology, Moscow," Mir, 2000, pp. 110-111 (with English translation).
Rudikoff et al., "Single amino acid substitution altering antigen-binding specificity," Proc. Nat. Acad. Sci. USA, 1982,79:1979-1983.
Yaghoub et al., "Antibody humanization methods—a review and update," Biotechnology and Genetic Engineering Reviews, Oct. 2013 29(2):175-186, XP055250530, ISSN: 0264-8725, DOI: 10.1080/02648725.2013.801235.

(Continued)

*Primary Examiner* — Lei Yao
(74) *Attorney, Agent, or Firm* — Fish & Richardson P.C.

(57) ABSTRACT

Provided are a LAG-3 antibody, an antigen-binding fragment thereof, and a pharmaceutical application thereof. Further, provided are a chimeric antibody comprising a CDR of the LAG-3 antibody, a humanized antibody, a pharmaceutical composition comprising the LAG-3 antibody and the antigen-binding fragment thereof, and an application of the pharmaceutical composition as an antineoplastic drug. Particularly, provided is an application of a humanized LAG-3 antibody in preparation of drugs for treatment of diseases involving immune cells.

21 Claims, 1 Drawing Sheet
Specification includes a Sequence Listing.

(56) References Cited

OTHER PUBLICATIONS

Gandhi et al., "Expression of LAG-3 by tumor-infiltrating lymphocytes is coincident with the suppression of latent membrane antigen—specific CD8 T-cell function in Hodgkin lymphoma patients", Blood, 108(7): 2280-9, 2006.

Goldberg et al., "LAG-3 in Cancer Immunotherapy", Curr. Top Microbiol. Immunol/ vol. 344, pp. 1-1, Dec. 30, 2015.

Grosso et al., "LAG-3 regulates CD8+ T cell accumulation and effector function in murine selfand tumor-tolerance systems", J Clin Invest, 117(11): 3383-92, 2007.

Haudebourg et al., "Depletion of LAG-3 Positive Cells in Cardiac Allograft Reveals Their Role in Rejection and Tolerance", Transplantation, 84(11): 1500-6, 2007.

Huang et al., "Role of LAG-3 in Regulatory T Cells", Immunity, 21(4): 503-13, 2004.

Huard et al., "Characterization of the major histocompatibility complex class II binding site on LAG-3 protein", Proc Natl Acad Sci USA, 94(11): 5744-9, 1997.

Jones et al., "The diversity of costimulatory and inhibitory receptor pathways and the regulation of antiviral T cell responses", Curr Opin Immunol, 21(2): 179-86, 2009.

Kisielow et al., "Expression of lymphocyte activation gene 3 (LAG-3) on B cells is induced by T cells", Eur J Immunol, 35 (7): 2081-8, 2005.

Triebel et al., "LAG-3, A Novel Lymphocyte Activation Gene Closely Related to CD4", J Exp Med, 171(5): 1393-405, 1990.

Workman et al., "LAG-3 Regulates Plasmacytoid Dendritic Cell Homeostasis1", J Immunol, 182(4): 1885-91, 2009.

Workman et al., "The CD4-related molecule, LAG-3 (CD223), regulates the expansion of activated T cells", Eur J Immunol, 33 (4): 970-9, 2003.

* cited by examiner

SEQUENCE LISTING

```
<160> NUMBER OF SEQ ID NOS: 39

<210> SEQ ID NO 1
<211> LENGTH: 442
<212> TYPE: PRT
<213> ORGANISM: Artificial sequence
<220> FEATURE:
<223> OTHER INFORMATION: LAG-3-Flag

<400> SEQUENCE: 1

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
                20                  25                  30

Trp Ala Gln Glu Gly Ala Pro Ala Gln Leu Pro Cys Ser Pro Thr Ile
            35                  40                  45

Pro Leu Gln Asp Leu Ser Leu Leu Arg Arg Ala Gly Val Thr Trp Gln
        50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95
```

-continued

```
Arg Arg Tyr Thr Val Leu Ser Val Gly Pro Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
    130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His Leu Ala Glu Ser
    210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
        275                 280                 285

Gly Thr Arg Ser Phe Leu Thr Ala Lys Trp Thr Pro Pro Gly Gly Gly
    290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365

Cys Glu Val Thr Pro Val Ser Gly Gln Glu Arg Phe Val Trp Ser Ser
    370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Asp Tyr Lys Asp Asp Asp Lys
        435                 440

<210> SEQ ID NO 2
<211> LENGTH: 525
<212> TYPE: PRT
<213> ORGANISM: Homo sapiens

<400> SEQUENCE: 2

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30
```

-continued

```
Trp Ala Gln Glu Gly Ala Pro Ala Gln Leu Pro Cys Ser Pro Thr Ile
         35                  40                  45
Pro Leu Gln Asp Leu Ser Leu Leu Arg Arg Ala Gly Val Thr Trp Gln
 50                  55                  60
His Gln Pro Asp Ser Gly Pro Pro Ala Ala Pro Gly His Pro Leu
 65                  70                  75                  80
Ala Pro Gly Pro His Pro Ala Ala Pro Ser Ser Trp Gly Pro Arg Pro
                 85                  90                  95
Arg Arg Tyr Thr Val Leu Ser Val Gly Pro Gly Leu Arg Ser Gly
                 100                 105                 110
Arg Leu Pro Leu Gln Pro Arg Val Gln Leu Asp Glu Arg Gly Arg Gln
             115                 120                 125
Arg Gly Asp Phe Ser Leu Trp Leu Arg Pro Ala Arg Arg Ala Asp Ala
         130                 135                 140
Gly Glu Tyr Arg Ala Ala Val His Leu Arg Asp Arg Ala Leu Ser Cys
145                 150                 155                 160
Arg Leu Arg Leu Arg Leu Gly Gln Ala Ser Met Thr Ala Ser Pro Pro
                 165                 170                 175
Gly Ser Leu Arg Ala Ser Asp Trp Val Ile Leu Asn Cys Ser Phe Ser
             180                 185                 190
Arg Pro Asp Arg Pro Ala Ser Val His Trp Phe Arg Asn Arg Gly Gln
         195                 200                 205
Gly Arg Val Pro Val Arg Glu Ser Pro His His Leu Ala Glu Ser
210                 215                 220
Phe Leu Phe Leu Pro Gln Val Ser Pro Met Asp Ser Gly Pro Trp Gly
225                 230                 235                 240
Cys Ile Leu Thr Tyr Arg Asp Gly Phe Asn Val Ser Ile Met Tyr Asn
                 245                 250                 255
Leu Thr Val Leu Gly Leu Glu Pro Pro Thr Pro Leu Thr Val Tyr Ala
             260                 265                 270
Gly Ala Gly Ser Arg Val Gly Leu Pro Cys Arg Leu Pro Ala Gly Val
         275                 280                 285
Gly Thr Arg Ser Phe Leu Thr Ala Lys Trp Thr Pro Pro Gly Gly Gly
         290                 295                 300
Pro Asp Leu Leu Val Thr Gly Asp Asn Gly Asp Phe Thr Leu Arg Leu
305                 310                 315                 320
Glu Asp Val Ser Gln Ala Gln Ala Gly Thr Tyr Thr Cys His Ile His
                 325                 330                 335
Leu Gln Glu Gln Gln Leu Asn Ala Thr Val Thr Leu Ala Ile Ile Thr
             340                 345                 350
Val Thr Pro Lys Ser Phe Gly Ser Pro Gly Ser Leu Gly Lys Leu Leu
         355                 360                 365
Cys Glu Val Thr Pro Val Ser Gly Gln Glu Arg Phe Val Trp Ser Ser
370                 375                 380
Leu Asp Thr Pro Ser Gln Arg Ser Phe Ser Gly Pro Trp Leu Glu Ala
385                 390                 395                 400
Gln Glu Ala Gln Leu Leu Ser Gln Pro Trp Gln Cys Gln Leu Tyr Gln
                 405                 410                 415
Gly Glu Arg Leu Leu Gly Ala Ala Val Tyr Phe Thr Glu Leu Ser Ser
             420                 425                 430
Pro Gly Ala Gln Arg Ser Gly Arg Ala Pro Gly Ala Leu Pro Ala Gly
         435                 440                 445
```

```
His Leu Leu Phe Leu Ile Leu Gly Val Leu Ser Leu Leu Leu
    450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
                485                 490                 495

Ser Lys Ile Glu Glu Leu Glu Gln Glu Pro Glu Pro Glu Pro Glu Pro
            500                 505                 510

Glu Pro Glu Pro Glu Pro Glu Pro Glu Gln Leu
            515                 520                 525

<210> SEQ ID NO 3
<211> LENGTH: 675
<212> TYPE: PRT
<213> ORGANISM: Artificial sequence
<220> FEATURE:
<223> OTHER INFORMATION: Fusion protein of LAG-3 extracellular region
      and hIgG1 Fc

<400> SEQUENCE: 3

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
    50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His Leu Ala Glu Ser
210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
        275                 280                 285
```

```
Gly Thr Arg Ser Phe Leu Thr Ala Lys Trp Thr Pro Gly Gly Gly
    290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365

Cys Glu Val Thr Pro Val Ser Gly Gln Glu Arg Phe Val Trp Ser Ser
370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Asp Asp Asp Lys Gly Ser Gly Ser Gly Glu Pro Lys Ser
        435                 440                 445

Cys Asp Lys Thr His Thr Cys Pro Pro Cys Pro Ala Pro Glu Leu Leu
450                 455                 460

Gly Gly Pro Ser Val Phe Leu Phe Pro Pro Lys Pro Lys Asp Thr Leu
465                 470                 475                 480

Met Ile Ser Arg Thr Pro Glu Val Thr Cys Val Val Asp Val Ser
                485                 490                 495

His Glu Asp Pro Glu Val Lys Phe Asn Trp Tyr Val Asp Gly Val Glu
            500                 505                 510

Val His Asn Ala Lys Thr Lys Pro Arg Glu Glu Gln Tyr Asn Ser Thr
        515                 520                 525

Tyr Arg Val Val Ser Val Leu Thr Val Leu His Gln Asp Trp Leu Asn
530                 535                 540

Gly Lys Glu Tyr Lys Cys Lys Val Ser Asn Lys Ala Leu Pro Ala Pro
545                 550                 555                 560

Ile Glu Lys Thr Ile Ser Lys Ala Lys Gly Gln Pro Arg Glu Pro Gln
                565                 570                 575

Val Tyr Thr Leu Pro Pro Ser Arg Glu Glu Met Thr Lys Asn Gln Val
            580                 585                 590

Ser Leu Thr Cys Leu Val Lys Gly Phe Tyr Pro Ser Asp Ile Ala Val
        595                 600                 605

Glu Trp Glu Ser Asn Gly Gln Pro Glu Asn Asn Tyr Lys Thr Thr Pro
610                 615                 620

Pro Val Leu Asp Ser Asp Gly Ser Phe Phe Leu Tyr Ser Lys Leu Thr
625                 630                 635                 640

Val Asp Lys Ser Arg Trp Gln Gln Gly Asn Val Phe Ser Cys Ser Val
                645                 650                 655

Met His Glu Ala Leu His Asn His Tyr Thr Gln Lys Ser Leu Ser Leu
            660                 665                 670

Ser Pro Gly
        675

<210> SEQ ID NO 4
<211> LENGTH: 677
```

<212> TYPE: PRT
<213> ORGANISM: Artificial sequence
<220> FEATURE:
<223> OTHER INFORMATION: Fusion protein of LAG-3 extracellular domain
      and mIgG2a Fc

<400> SEQUENCE: 4

```
Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Arg Arg Ala Gly Val Thr Trp Gln
    50                  55                  60

His Gln Pro Asp Ser Gly Pro Pro Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
    130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His Leu Ala Glu Ser
    210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
        275                 280                 285

Gly Thr Arg Ser Phe Leu Thr Ala Lys Trp Thr Pro Gly Gly Gly
    290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365

Cys Glu Val Thr Pro Val Ser Gly Gln Glu Arg Phe Val Trp Ser Ser
    370                 375                 380
```

```
Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
            405                 410                 415

Gly Glu Arg Leu Leu Gly Ala Ala Val Tyr Phe Thr Glu Leu Ser Ser
        420                 425                 430

Pro Gly Asp Asp Asp Asp Lys Gly Ser Gly Ser Gly Glu Pro Arg Gly
    435                 440                 445

Pro Thr Ile Lys Pro Cys Pro Pro Cys Lys Cys Pro Ala Pro Asn Leu
450                 455                 460

Leu Gly Gly Pro Ser Val Phe Ile Phe Pro Pro Lys Ile Lys Asp Val
465                 470                 475                 480

Leu Met Ile Ser Leu Ser Pro Ile Val Thr Cys Val Val Asp Val
            485                 490                 495

Ser Glu Asp Asp Pro Asp Val Gln Ile Ser Trp Phe Val Asn Asn Val
                500                 505                 510

Glu Val His Thr Ala Gln Thr Gln Thr His Arg Glu Asp Tyr Asn Ser
        515                 520                 525

Thr Leu Arg Val Val Ser Ala Leu Pro Ile Gln His Gln Asp Trp Met
        530                 535                 540

Ser Gly Lys Glu Phe Lys Cys Lys Val Asn Asn Lys Asp Leu Pro Ala
545                 550                 555                 560

Pro Ile Glu Arg Thr Ile Ser Lys Pro Lys Gly Ser Val Arg Ala Pro
                565                 570                 575

Gln Val Tyr Val Leu Pro Pro Pro Glu Glu Met Thr Lys Lys Gln
        580                 585                 590

Val Thr Leu Thr Cys Met Val Thr Asp Phe Met Pro Glu Asp Ile Tyr
        595                 600                 605

Val Glu Trp Thr Asn Asn Gly Lys Thr Glu Leu Asn Tyr Lys Asn Thr
610                 615                 620

Glu Pro Val Leu Asp Ser Asp Gly Ser Tyr Phe Met Tyr Ser Lys Leu
625                 630                 635                 640

Arg Val Glu Lys Lys Asn Trp Val Glu Arg Asn Ser Tyr Ser Cys Ser
                645                 650                 655

Val Val His Glu Gly Leu His Asn His His Thr Thr Lys Ser Phe Ser
            660                 665                 670

Arg Thr Pro Gly Lys
        675

<210> SEQ ID NO 5
<211> LENGTH: 124
<212> TYPE: PRT
<213> ORGANISM: Mus musculus

<400> SEQUENCE: 5

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Thr Ser
            20                  25                  30

Gly Met Ser Trp Val Lys Gln Ala Pro Gly Lys Gly Leu Lys Trp Met
        35                  40                  45

Gly Trp Ile Asn Thr Tyr Ser Gly Val Pro Tyr Ala Asp Asp Phe
    50                  55                  60

Lys Gly Arg Phe Ala Phe Ser Leu Glu Thr Ser Ala Ser Thr Ala Tyr
```

65                  70                  75                  80
Leu Gln Ile Asn Asn Leu Lys Asn Glu Asp Thr Ala Thr Tyr Phe Cys
                85                  90                  95
Ala Arg Asp Asn Tyr Asp Ala Arg Asp Val Tyr Tyr Tyr Ala Met Asp
                100                 105                 110
Tyr Trp Gly Gln Gly Thr Ser Val Thr Val Ser Ser
            115                 120

<210> SEQ ID NO 6
<211> LENGTH: 107
<212> TYPE: PRT
<213> ORGANISM: Mus musculus

<400> SEQUENCE: 6

Asp Ile Gln Met Thr Gln Ser Pro Ala Ser Leu Ser Val Ser Val Gly
1               5                   10                  15
Glu Thr Val Thr Ile Thr Cys Arg Ala Ser Glu Asn Ile Tyr Ser Asn
                20                  25                  30
Leu Ala Trp Tyr Gln Gln Lys Gln Gly Lys Ser Pro Gln Leu Leu Val
            35                  40                  45
Tyr Ala Ala Thr Asn Leu Ala Asp Gly Val Pro Ser Arg Phe Ser Gly
        50                  55                  60
Ser Gly Ser Gly Thr Gln Tyr Ser Leu Lys Ile Asn Ser Leu Gln Ser
65                  70                  75                  80
Glu Asp Phe Gly Ser Tyr Tyr Cys Gln His Phe Trp Ile Thr Pro Trp
                85                  90                  95
Thr Phe Gly Gly Gly Thr Lys Leu Glu Ile Lys
                100                 105

<210> SEQ ID NO 7
<211> LENGTH: 120
<212> TYPE: PRT
<213> ORGANISM: Mus musculus

<400> SEQUENCE: 7

Glu Val Gln Leu Gln Gln Ser Gly Pro Val Leu Val Lys Pro Gly Ala
1               5                   10                  15
Ser Val Lys Met Ser Cys Lys Ala Ser Gly Tyr Thr Leu Thr Asp Tyr
                20                  25                  30
Tyr Met Asn Trp Val Lys Gln Ser His Gly Lys Ser Leu Glu Trp Ile
            35                  40                  45
Gly Val Ile Asn Pro Tyr Asn Gly Asp Thr Ala Tyr Asn Gln Lys Phe
        50                  55                  60
Lys Gly Lys Ala Thr Leu Thr Val Asp Lys Ser Ser Asn Thr Ala Tyr
65                  70                  75                  80
Met Glu Ile Asn Ser Leu Thr Ser Glu Asp Ser Ala Val Tyr Tyr Cys
                85                  90                  95
Thr Arg Asp Asp Gly Tyr Tyr Asp Tyr Tyr Phe Asp Val Trp Gly Thr
                100                 105                 110
Gly Thr Thr Val Thr Val Ser Ser
            115                 120

<210> SEQ ID NO 8
<211> LENGTH: 107
<212> TYPE: PRT
<213> ORGANISM: Mus musculus

<400> SEQUENCE: 8

```
Asp Ile Gln Met Thr Gln Ser Pro Ser Ser Leu Ser Ala Ser Leu Gly
1               5                   10                  15

Glu Arg Val Ile Leu Thr Cys Arg Ala Ser Gln Asp Ile Gly Ser Arg
            20                  25                  30

Leu Asn Trp Leu Gln Gln Gly Pro Asp Gly Thr Phe Lys Arg Leu Ile
            35                  40                  45

Tyr Ala Thr Ser Thr Leu Asp Ser Gly Val Pro Lys Arg Phe Ser Gly
50                  55                  60

Ser Arg Ser Gly Ser Asp Phe Ser Leu Thr Ile Ser Ser Leu Glu Ser
65                  70                  75                  80

Glu Asp Phe Val Asp Tyr Tyr Cys Leu Gln Leu Ala Ser Ser Pro Pro
                85                  90                  95

Thr Phe Gly Gly Gly Thr Lys Leu Glu Ile Lys
                100                 105
```

<210> SEQ ID NO 9
<211> LENGTH: 5
<212> TYPE: PRT
<213> ORGANISM: Mus musculus

<400> SEQUENCE: 9

```
Thr Ser Gly Met Ser
1               5
```

<210> SEQ ID NO 10
<211> LENGTH: 17
<212> TYPE: PRT
<213> ORGANISM: Mus musculus

<400> SEQUENCE: 10

```
Trp Ile Asn Thr Tyr Ser Gly Val Pro Thr Tyr Ala Asp Asp Phe Lys
1               5                   10                  15

Gly
```

<210> SEQ ID NO 11
<211> LENGTH: 15
<212> TYPE: PRT
<213> ORGANISM: Mus musculus

<400> SEQUENCE: 11

```
Asp Asn Tyr Asp Ala Arg Asp Val Tyr Tyr Ala Met Asp Tyr
1               5                   10                  15
```

<210> SEQ ID NO 12
<211> LENGTH: 5
<212> TYPE: PRT
<213> ORGANISM: Mus musculus

<400> SEQUENCE: 12

```
Asp Tyr Tyr Met Asn
1               5
```

<210> SEQ ID NO 13
<211> LENGTH: 17
<212> TYPE: PRT
<213> ORGANISM: Mus musculus

<400> SEQUENCE: 13

```
Val Ile Asn Pro Tyr Asn Gly Asp Thr Ala Tyr Asn Gln Lys Phe Lys
1               5                   10                  15
```

Gly

<210> SEQ ID NO 14
<211> LENGTH: 11
<212> TYPE: PRT
<213> ORGANISM: Mus musculus

<400> SEQUENCE: 14

Asp Asp Gly Tyr Tyr Asp Tyr Tyr Phe Asp Val
1               5                   10

<210> SEQ ID NO 15
<211> LENGTH: 11
<212> TYPE: PRT
<213> ORGANISM: Mus musculus

<400> SEQUENCE: 15

Arg Ala Ser Glu Asn Ile Tyr Ser Asn Leu Ala
1               5                   10

<210> SEQ ID NO 16
<211> LENGTH: 7
<212> TYPE: PRT
<213> ORGANISM: Mus musculus

<400> SEQUENCE: 16

Ala Ala Thr Asn Leu Ala Asp
1               5

<210> SEQ ID NO 17
<211> LENGTH: 9
<212> TYPE: PRT
<213> ORGANISM: Mus musculus

<400> SEQUENCE: 17

Gln His Phe Trp Ile Thr Pro Trp Thr
1               5

<210> SEQ ID NO 18
<211> LENGTH: 11
<212> TYPE: PRT
<213> ORGANISM: Mus musculus

<400> SEQUENCE: 18

Arg Ala Ser Gln Asp Ile Gly Ser Arg Leu Asn
1               5                   10

<210> SEQ ID NO 19
<211> LENGTH: 7
<212> TYPE: PRT
<213> ORGANISM: Mus musculus

<400> SEQUENCE: 19

Ala Thr Ser Thr Leu Asp Ser
1               5

<210> SEQ ID NO 20
<211> LENGTH: 9
<212> TYPE: PRT
<213> ORGANISM: Mus musculus

<400> SEQUENCE: 20

Leu Gln Leu Ala Ser Ser Pro Pro Thr
1               5

-continued

<210> SEQ ID NO 21
<211> LENGTH: 124
<212> TYPE: PRT
<213> ORGANISM: Artificial sequence
<220> FEATURE:
<223> OTHER INFORMATION: Hu229VH.1

<400> SEQUENCE: 21

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Thr Ser
            20                  25                  30

Gly Met Ser Trp Val Arg Gln Ala Pro Gly Gln Gly Leu Glu Trp Met
        35                  40                  45

Gly Trp Ile Asn Thr Tyr Ser Gly Val Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Asn Tyr Asp Ala Arg Asp Val Tyr Tyr Ala Met Asp
            100                 105                 110

Tyr Trp Gly Gln Gly Thr Thr Val Thr Val Ser Ser
        115                 120

<210> SEQ ID NO 22
<211> LENGTH: 107
<212> TYPE: PRT
<213> ORGANISM: Artificial sequence
<220> FEATURE:
<223> OTHER INFORMATION: Hu229VL.1

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Ala Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Trp Ile Thr Pro Trp
                85                  90                  95

Thr Phe Gly Gly Gly Thr Lys Val Glu Ile Lys
            100                 105

<210> SEQ ID NO 23
<211> LENGTH: 124
<212> TYPE: PRT
<213> ORGANISM: Artificial sequence
<220> FEATURE:
<223> OTHER INFORMATION: Hu229VH.1A

<400> SEQUENCE: 23

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Thr Ser

```
            20                  25                  30
Gly Met Ser Trp Val Arg Gln Ala Pro Gly Gln Gly Leu Lys Trp Met
        35                  40                  45

Gly Trp Ile Asn Thr Tyr Ser Gly Val Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Asn Tyr Asp Ala Arg Asp Val Tyr Tyr Tyr Ala Met Asp
            100                 105                 110

Tyr Trp Gly Gln Gly Thr Thr Val Thr Val Ser Ser
            115                 120

<210> SEQ ID NO 24
<211> LENGTH: 124
<212> TYPE: PRT
<213> ORGANISM: Artificial sequence
<220> FEATURE:
<223> OTHER INFORMATION: Hu229VH.1B

<400> SEQUENCE: 24

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Thr Ser
            20                  25                  30

Gly Met Ser Trp Val Lys Gln Ala Pro Gly Gln Gly Leu Lys Trp Met
        35                  40                  45

Gly Trp Ile Asn Thr Tyr Ser Gly Val Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Tyr Tyr Tyr Cys
                85                  90                  95

Ala Arg Asp Asn Tyr Asp Ala Arg Asp Val Tyr Tyr Tyr Ala Met Asp
            100                 105                 110

Tyr Trp Gly Gln Gly Thr Thr Val Thr Val Ser Ser
            115                 120

<210> SEQ ID NO 25
<211> LENGTH: 124
<212> TYPE: PRT
<213> ORGANISM: Artificial sequence
<220> FEATURE:
<223> OTHER INFORMATION: Hu229VH.1C

<400> SEQUENCE: 25

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Thr Ser
            20                  25                  30

Gly Met Ser Trp Val Lys Gln Ala Pro Gly Gln Gly Leu Lys Trp Met
        35                  40                  45

Gly Trp Ile Asn Thr Tyr Ser Gly Val Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80
```

```
Leu Gln Ile Ser Ser Leu Lys Ala Glu Asp Thr Ala Thr Tyr Phe Cys
            85                  90                  95

Ala Arg Asp Asn Tyr Asp Ala Arg Asp Val Tyr Tyr Tyr Ala Met Asp
        100                 105                 110

Tyr Trp Gly Gln Gly Thr Thr Val Thr Val Ser Ser
        115                 120

<210> SEQ ID NO 26
<211> LENGTH: 107
<212> TYPE: PRT
<213> ORGANISM: Artificial sequence
<220> FEATURE:
<223> OTHER INFORMATION: Hu229VL.1A

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Ile Thr Pro Trp
                85                  90                  95

Thr Phe Gly Gly Gly Thr Lys Val Glu Ile Lys
        100                 105

<210> SEQ ID NO 27
<211> LENGTH: 107
<212> TYPE: PRT
<213> ORGANISM: Artificial sequence
<220> FEATURE:
<223> OTHER INFORMATION: Hu229VL.1B

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Thr Leu Thr Ile Ser Ser Leu Gln Pro
65                  70                  75                  80

Glu Asp Phe Ala Thr Tyr Tyr Cys Gln His Phe Trp Ile Thr Pro Trp
                85                  90                  95

Thr Phe Gly Gly Gly Thr Lys Val Glu Ile Lys
        100                 105

<210> SEQ ID NO 28
<211> LENGTH: 107
<212> TYPE: PRT
<213> ORGANISM: Artificial sequence
<220> FEATURE:
<223> OTHER INFORMATION: Hu229VL.1C
```

```
<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ser Pro Lys Leu Leu Val
        35                  40                  45

Tyr Ala Ala Thr Asn Leu Ala Asp Gly Val Pro Ser Arg Phe Ser Gly
50                  55                  60

Ser Gly Ser Gly Thr Gln Tyr Thr Leu Thr Ile Ser Ser Leu Gln Pro
65                  70                  75                  80

Glu Asp Phe Ala Thr Tyr Tyr Cys Gln His Phe Trp Ile Thr Pro Trp
                85                  90                  95

Thr Phe Gly Gly Gly Thr Lys Val Glu Ile Lys
            100                 105

<210> SEQ ID NO 29
<211> LENGTH: 120
<212> TYPE: PRT
<213> ORGANISM: Artificial sequence
<220> FEATURE:
<223> OTHER INFORMATION: Hu303_VH.1

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Arg Leu Glu Trp Met
        35                  40                  45

Gly Val Ile Asn Pro Tyr Asn Gly Asp Thr Ala Tyr Asn Gln Lys Phe
50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asp Gly Tyr Tyr Asp Tyr Tyr Phe Asp Val Trp Gly Gln
            100                 105                 110

Gly Thr Thr Val Thr Val Ser Ser
        115                 120

<210> SEQ ID NO 30
<211> LENGTH: 107
<212> TYPE: PRT
<213> ORGANISM: Artificial sequence
<220> FEATURE:
<223> OTHER INFORMATION: Hu303_VL.1

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Ser Arg
            20                  25                  30

Leu Asn Trp Tyr Gln Gln Lys Pro Gly Lys Ala Pro Lys Leu Leu Ile
        35                  40                  45

Tyr Ala Thr Ser Thr Leu Asp Ser Gly Val Pro Ser Arg Phe Ser Gly
50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Leu Ala Ser Ser Pro Pro
                 85                  90                  95

Thr Phe Gly Gly Gly Thr Lys Val Glu Ile Lys
                100                 105

<210> SEQ ID NO 31
<211> LENGTH: 120
<212> TYPE: PRT
<213> ORGANISM: Artificial sequence
<220> FEATURE:
<223> OTHER INFORMATION: Hu303_VH.1A

<400> SEQUENCE: 31

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
                20                  25                  30

Tyr Met Asn Trp Val Arg Gln Ala Pro Gly Gln Arg Leu Glu Trp Met
             35                  40                  45

Gly Val Ile Asn Pro Tyr Asn Gly Asp Thr Ala Tyr Asn Gln Lys Phe
         50                  55                  60

Lys Gly Arg Val Thr Ile Thr Val Asp Lys Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Thr Arg Asp Asp Gly Tyr Tyr Asp Tyr Tyr Phe Asp Val Trp Gly Gln
                100                 105                 110

Gly Thr Thr Val Thr Val Ser Ser
            115                 120

<210> SEQ ID NO 32
<211> LENGTH: 120
<212> TYPE: PRT
<213> ORGANISM: Artificial sequence
<220> FEATURE:
<223> OTHER INFORMATION: Hu303_VH.1B

<400> SEQUENCE: 32

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Leu Thr Asp Tyr
                20                  25                  30

Tyr Met Asn Trp Val Arg Gln Ala Pro Gly Gln Arg Leu Glu Trp Met
             35                  40                  45

Gly Val Ile Asn Pro Tyr Asn Gly Asp Thr Ala Tyr Asn Gln Lys Phe
         50                  55                  60

Lys Gly Arg Val Thr Ile Thr Val Asp Lys Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Thr Arg Asp Asp Gly Tyr Tyr Asp Tyr Tyr Phe Asp Val Trp Gly Gln
                100                 105                 110

Gly Thr Thr Val Thr Val Ser Ser
            115                 120

<210> SEQ ID NO 33
```

```
<211> LENGTH: 120
<212> TYPE: PRT
<213> ORGANISM: Artificial sequence
<220> FEATURE:
<223> OTHER INFORMATION: Hu303_VH.1C

<400> SEQUENCE: 33
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Asp Tyr
            20                  25                  30

Tyr Met Asn Trp Val Arg Gln Ala Pro Gly Gln Arg Leu Glu Trp Ile
        35                  40                  45

Gly Val Ile Asn Pro Tyr Asn Gly Asp Thr Ala Tyr Asn Gln Lys Phe
    50                  55                  60

Lys Gly Arg Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Asp Asp Gly Tyr Tyr Asp Tyr Tyr Phe Asp Val Trp Gly Gln
            100                 105                 110

Gly Thr Thr Val Thr Val Ser Ser
            115                 120

```
<210> SEQ ID NO 34
<211> LENGTH: 107
<212> TYPE: PRT
<213> ORGANISM: Artificial sequence
<220> FEATURE:
<223> OTHER INFORMATION: Hu303_VL.1A

<400> SEQUENCE: 34
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Ser Arg
            20                  25                  30

Leu Asn Trp Tyr Gln Gln Lys Pro Gly Lys Ala Pro Lys Arg Leu Ile
        35                  40                  45

Tyr Ala Thr Ser Thr Leu Asp Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Leu Gln Leu Ala Ser Ser Pro Pro
                85                  90                  95

Thr Phe Gly Gly Gly Thr Lys Val Glu Ile Lys
            100                 105

```
<210> SEQ ID NO 35
<211> LENGTH: 107
<212> TYPE: PRT
<213> ORGANISM: Artificial sequence
<220> FEATURE:
<223> OTHER INFORMATION: Hu303_VL.1B

<400> SEQUENCE: 35
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Ser Arg
            20                  25                  30

Leu Asn Trp Tyr Gln Gln Lys Pro Gly Lys Ala Pro Lys Arg Leu Ile
         35                  40                  45

Tyr Ala Thr Ser Thr Leu Asp Ser Gly Val Pro Lys Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Leu Gln Leu Ala Ser Ser Pro Pro
                 85                  90                  95

Thr Phe Gly Gly Gly Thr Lys Val Glu Ile Lys
                100                 105

<210> SEQ ID NO 36
<211> LENGTH: 107
<212> TYPE: PRT
<213> ORGANISM: Artificial sequence
<220> FEATURE:
<223> OTHER INFORMATION: Hu303_VL.1C

<400> SEQUENCE: 36

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Gly Ser Arg
                 20                  25                  30

Leu Asn Trp Leu Gln Gln Lys Pro Gly Lys Ala Phe Lys Arg Leu Ile
         35                  40                  45

Tyr Ala Thr Ser Thr Leu Asp Ser Gly Val Pro Lys Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Leu Gln Leu Ala Ser Ser Pro Pro
                 85                  90                  95

Thr Phe Gly Gly Gly Thr Lys Val Glu Ile Lys
                100                 105

<210> SEQ ID NO 37
<211> LENGTH: 107
<212> TYPE: PRT
<213> ORGANISM: Artificial sequence
<220> FEATURE:
<223> OTHER INFORMATION: Hu303_VL.1D

<400> SEQUENCE: 37

Asp Ile Gln Met Thr Gln Ser Pro Ser Ser Leu Ser Ala Ser Val Gly
 1               5                  10                  15

Asp Arg Val Thr Leu Thr Cys Arg Ala Ser Gln Asp Ile Gly Ser Arg
                 20                  25                  30

Leu Asn Trp Leu Gln Gln Lys Pro Gly Gly Ala Phe Lys Arg Leu Ile
         35                  40                  45

Tyr Ala Thr Ser Thr Leu Asp Ser Gly Val Pro Lys Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Asp Tyr Tyr Cys Leu Gln Leu Ala Ser Ser Pro Pro
                 85                  90                  95

Thr Phe Gly Gly Gly Thr Lys Val Glu Ile Lys
                100                 105

<210> SEQ ID NO 38

<211> LENGTH: 327
<212> TYPE: PRT
<213> ORGANISM: Artificial sequence
<220> FEATURE:
<223> OTHER INFORMATION: Constant region of heavy chain, S228P mutation

<400> SEQUENCE: 38

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 39
<211> LENGTH: 107
<212> TYPE: PRT
<213> ORGANISM: Artificial sequence
<220> FEATURE:
<223> OTHER INFORMATION: Constant region of light chain kappa

```
<400> SEQUENCE: 39

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

LAG-3 ANTIBODY, ANTIGEN-BINDING FRAGMENT THEREOF, AND PHARMACEUTICAL APPLICATION THEREOF

CROSS-REFERENCE TO RELATED APPLICATIONS

This application is a National Stage Application under 35 U.S.C. § 371 and claims the benefit of International Application No. PCT/CN2017/089492, filed Jun. 22, 2017, which claims priority to Chinese Application No. CN201610465386.2, filed Jun. 23, 2016. The disclosures of the foregoing applications are hereby incorporated by reference in their entirety.

FIELD OF THE INVENTION

The present invention relates to a LAG-3 antibody, antigen-binding fragment thereof, a chimeric antibody or a humanized antibody comprising the CDR regions of the LAG-3 antibody, as well as pharmaceutical compositions comprising the LAG-3 antibody and the antigen-binding fragment thereof, as well as its use as an anti-cancer drug.

BACKGROUND OF THE INVENTION

Lymphocyte Activation Gene-3, also known as LAG-3 or CD223, is a member of the immunoglobulin superfamily, which can negatively regulate various functions and survival cycles of immune cells. Studies have shown that LAG-3 plays an important role in viral infection, autoimmune diseases and tumor-induced immune system dysfunction. Influencing the function of LAG-3 can improve the status of immune dysfunction during the development of these diseases, so as to improve the prognosis of the diseases.

As a member of the immunoglobulin superfamily, LAG-3 is composed of three regions: extracellular domain, transmembrane region and the cytoplasmic domain. The mature LAG-3 molecule, which was first discovered by Triebel et al. in 1990 (J Exp Med, 1990, 171 (5): 1393-405), consists of 470 amino acids with a relative molecular weight of 70 kDa. It has been found that LAG-3, like CTLA-4 and PD-1, is a negative co-stimulatory molecule, the activation of which can negatively regulate function of lymphocyte. Structurally, LAG-3 is closely related to CD4, but it has reverse function to CD4. For example, LAG-3 molecule has high similarity to CD4 molecule, and both can bind to MHC-II (Major Histocompatibility Complex) class molecules. However, the binding avidity of LAG-3 to MHC-II molecules is higher than that of CD4. Thus, it intervenes in TCR activation induced by CD4$^+$T lymphocyte cells and inhibits the activation of T lymphocyte (Curr Opin Immunol, 2009, 21(2):179-86; Eur J Immunol, 2003, 33 (4): 970-9). In vitro studies, it has been shown that LAG-3 can inhibit the proliferation of T lymphocyte induced by antigen. Blocking LAG-3 will improve activation and proliferation of T lymphocyte, and improve the cytokines secreted by type 1 T helper cells (Th1). Huang et al. have showed that the level of LAG-3 on the activated CD4+ Treg cells was significantly increased, and LAG-3 was a necessary condition for CD4$^+$ Tregs to exert the greatest immunosuppressive effect (Immunity, 2004, 21 (4): 503-13). In addition, anti-LAG-3 antibody also maintains the homeostasis of CD4$^+$ and CD8$^+$T lymphocyte, blocking LAG-3 will significantly enhance the ability of CD8$^+$T lymphocytes to kill tumor cells (J Clin Invest, 2007, 117 (11): 3383-92). Some studies on diseases have also indicated that LAG-3 plays an important role in the regulating development and progression of a disease. Gandhi et al. verified that the expression level of LAG-3 in T lymphocytes of human lymphoma tissue is associated with T lymphocyte dysfunction, and clearance of LAG-3$^+$T lymphocytes can significantly enhance the ability of eliminating tumor cell by T lymphocytes (Blood, 2006, 108 (7): 2280-9). The results show that LAG-3 is an important inhibitory molecule on the surface of immune cells and has a significant negative regulatory effect on T lymphocytes.

LAG-3 is mainly expressed on T lymphocytes, B lymphocytes, NK cells, Treg cells and DC cells (Proc Natl Acad Sci USA, 1997, 94 (11): 5744-9. Eur J Immunol, 2005, 35 (7): 2081-8; J Immunol, 2009, 182 (4): 1885-91). LAG-3 is a class of immunosuppressive molecules, and is one of the components constituting the co-receptor of TCR. It intervenes in TCR activation induced by T lymphocyte, and plays a negatively regulatory role in the activation of T lymphocytes. In some diseases, the expression of LAG-3 was increased, and the corresponding immunosuppression was observed. Gandhi et al. found that the lymphocytes in the blood and tumor tissues from patients with Hoggkin's lymphoma highly expressed LAG-3; and the function of specific CD8$^+$T cells was obviously impaired in tumor tissues, if the LAG-3-positive T cell was removed, the anti-tumor function was restored and cytokine secretion was increased. It was speculated that the expression of LAG-3 is associated with the negative regulation of the immune function of specific T cells, inhibiting the function of LAG-3 molecule can enhance the anti-tumor effect of T cell, so that LAG-3 molecule may be a potential target for tumor immunotherapy (Blood, 2006, 108 (7): 2280-9).

Currently there are several multinational pharmaceutical companies, such as BMS and Novartis, engaging in the study of monoclonal antibodies against LAG-3, which enhance the anti-tumor effect of T cells and maximize the patients' own immune response to the tumor by stimulating antigen-specific T cell responses, and subsequently achieve the purpose to kill tumor cells. The currently relating patents are, such as WO2010019570, WO2014008218, WO9530750, WO2004078928, WO2008132601, WO2014140180 and WO2015138920.

The present invention provides a LAG-3 antibody with high affinity, high selectivity, and high biological activity.

SUMMARY OF THE INVENTION

The present invention provides a LAG-3 antibody or an antigen-binding fragment thereof, comprising any one or more of the CDR region selected from the following (i) or (ii) or sequences with at least 85% identity(preferably 95%) to the following:

(i) HCDR regions as shown in SEQ ID NO: 9, SEQ ID NO: 10 and SEQ ID NO: 11; and LCDR regions as shown in SEQ ID NO: 15, SEQ ID NO: 16 and SEQ ID NO: 17; or (ii) HCDR regions as shown in: SEQ ID NO: 12, SEQ ID NO: 13 and SEQ ID NO: 14; and LCDR regions as shown in SEQ ID NO: 18, SEQ ID NO: 19 and SEQ ID NO: 20.

In another preferred embodiment of the present invention, provided the LAG-3 antibody or the antigen-binding fragment thereof according to the present invention, wherein the heavy chain variable region comprises HCDR1, HCDR2 and HCDR3 as shown in SEQ ID NO:9, SEQ ID NO:10 and SEQ ID NO: 11, respectively, or sequences with at least 85% (preferably 95%) identity to these sequences.

In another preferred embodiment of the present invention, provided the LAG-3 antibody or antigen-binding fragment thereof according to the present invention, wherein the heavy chain variable region comprises HCDR1, HCDR2 and HCDR3 as shown in SEQ ID NO: 12, SEQ ID NO: 13 and SEQ ID NO: 14, respectively, or sequences with at least 85% (preferably 95%) identity to these sequences.

In another preferred embodiment of the present invention, provided the LAG-3 antibody or the antigen-binding fragment thereof according to the present invention, wherein the light chain variable region comprises LCDR1, LCDR2 and LCDR3 as shown in SEQ ID NO: 15, SEQ ID NO: 16 and SEQ ID NO: 17, respectively, or sequences with at least 85% (preferably 95%) identity to these sequences;

In another preferred embodiment of the present invention, provided the LAG-3 antibody or the antigen-binding fragment thereof according to the present invention, wherein the light chain variable region comprises LCDR1, LCDR2 and LCDR3 as shown in SEQ ID NO: 18, SEQ ID NO: 19 and SEQ ID NO: 20, respectively, or sequences with at least 85% (preferably 95%) identity to these sequences.

In another preferred embodiment of the present invention, provided the LAG-3 antibody or the antigen-binding fragment thereof according to the present invention, wherein the antibody or the antigen-binding fragment thereof is a murine antibody or a fragment thereof.

In another preferred embodiment of the present invention, provided the LAG-3 antibody or the antigen-binding fragment thereof according to the present invention, wherein the antibody light chain variable region further comprises light chain FR region derived from murine κ chain or a variant thereof, or light chain FR region derived from murine λ chain or a variant thereof; wherein the antibody heavy chain variable region further comprises heavy chain FR region derived from murine IgG1 or a variant thereof, or heavy chain FR region derived from murine IgG2 or a variant thereof, or heavy chain FR region derived from murine IgG3 or a variant thereof.

In another preferred embodiment of the present invention, provided a murine LAG-3 antibody or antigen-binding fragment thereof according to the present invention, wherein the murine antibody comprises a heavy chain variable region as shown in SEQ ID NO: 5 and a light chain variable region as shown in SEQ ID NO: 6.

In another preferred embodiment of the present invention, provided a murine LAG-3 antibody or the antigen-binding fragment thereof according to the present invention, wherein the murine antibody comprises a heavy chain variable region as shown in SEQ ID NO: 7 and a light chain variable region as shown in SEQ ID NO: 8.

In another preferred embodiment of the present invention, provided the LAG-3 antibody or the antigen-binding fragment thereof according to the present invention, wherein the antibody light chain further comprises light chain constant region derived from murine κ chain or a variant thereof, or light chain constant region derived from murine λ chain or a variant thereof; wherein the antibody heavy chain variable region further comprises heavy chain FR region derived from murine IgG1 or a variant thereof, or heavy chain FR region derived from murine IgG2 or a variant thereof, or heavy chain FR region derived from murine IgG3 or a variant thereof.

In another preferred embodiment of the present invention, provided the LAG-3 antibody or antigen-binding fragment thereof according to the present invention, wherein the antibody or the antigen-binding fragment thereof is a chimeric antibody or a fragment thereof.

In another preferred embodiment of the present invention, provided the LAG-3 antibody or antigen-binding fragment thereof according to the present invention, wherein the antibody or the antigen-binding fragment thereof is a humanized antibody or a fragment thereof.

In another preferred embodiment of the present invention, provided the LAG-3 antibody or the antigen-binding fragment thereof according to the present invention, wherein the heavy chain FR sequence of the heavy chain variable region of the humanized antibody is derived from a combination sequence of human germline heavy chain IGHV7-4-1*02 and hjh6.1, or derived from mutant sequence thereof; It comprises FR1, FR2, FR3 from human germline heavy chain IGHV7-4-1*02 and FR4 from hjh6.1, or the mutant sequence thereof; preferably, the heavy chain FR sequence of the humanized antibody has 0-10 amino acid back-mutations, more preferably has one or more back-mutations selected from the group consisting of E46K, R38K, V93T and Y95F.

In another preferred embodiment of the present invention, provided the LAG-3 antibody or antigen-binding fragment thereof according to the present invention, wherein the humanized antibody heavy chain variable region sequence is as shown in SEQ ID NO: 21, or a sequence with at least 85% (preferably 95%) identity to the sequence; preferably there are 1-10 amino acid changes in the heavy chain variable region. These amino acid changes may be made based on technology of affinity maturation in the art.

In another preferred embodiment of the present invention, provided the LAG-3 antibody or the antigen-binding fragment thereof according to the present invention, wherein humanized antibody heavy chain variable region comprises the sequence of SEQ ID NO: 21, SEQ ID NO: 23, SEQ ID NO: 24 or SEQ ID NO: 25, or a sequence with at least 85% (preferably 95%) identity to these sequences.

In another preferred embodiment of the present invention, provided the LAG-3 antibody or the antigen-binding fragment thereof according to the present invention, wherein the heavy chain FR sequence of the heavy chain variable region of the humanized antibody is derived from a combination sequence of human germline heavy chain IGHV1-3*01 and hjh6.1, or mutant sequences thereof; preferably it comprises FR1, FR2, FR3 from human germline heavy chain IGHV1-3*01 and FR4 from hjh6.1, or the mutant sequence thereof; wherein the heavy chain FR sequence of the humanized antibody has 0-10 amino acid back-mutations, more preferably one or more back-mutations selected from the group consisting of F29L, A97T, M48I, V68A, I70L, R72V and T74K.

In another preferred embodiment of the present invention, provided a humanized LAG-3 antibody or antigen-binding fragments thereof according to the present invention, wherein the humanized antibody heavy chain variable region sequence is as shown in SEQ ID NO: 29, or a sequence with at least 85% (preferably 95%) identity to the above sequence; preferably there are 1-10 amino acid changes in the heavy chain variable region; These amino acid changes may be made based on technology of affinity maturation in the art.

In another preferred embodiment of the present invention, provided the humanized LAG-3 antibody or the antigen-binding fragment thereof according to the present invention, wherein the heavy chain variable region sequence of the humanized antibody is selected from the sequences of SEQ ID NO: 29, SEQ ID NO: 31, SEQ ID NO: 32 or SEQ ID NO: 33, or a sequence with at least 85% (preferably 95%) identity to these sequences.

In another preferred embodiment of the present invention, provided the humanized LAG-3 antibody or the antigen-binding fragment thereof according to the present invention, wherein the light chain FR sequence of the humanized antibody light chain variable region is derived from a combination sequence of human germline light chain IGKV1-39*01 and hjk4.1 and the mutant sequences thereof, it comprises FR1, FR2, FR3 from human germline light chain IGKV1-39*01, and FR4 from hjk4.1 and the mutant sequence thereof.

In another preferred embodiment of the present invention, provided the humanized LAG-3 antibody or the antigen-binding fragment thereof according to the present invention, wherein the light chain variable region sequence of the humanized antibody is as shown in SEQ ID NO: 22, or a sequence with at least 85% identity to this sequence; preferably there are 1-10 amino acid changes in the light chain variable region. These amino acid changes may be made based on technology of affinity maturation in the art.

In another preferred embodiment of the present invention, provided the humanized LAG-3 antibody or the antigen-binding fragment thereof according to the present invention, wherein the light chain FR sequence of the humanized antibody has 0-10 amino acid back-mutations, preferably has one or more back-mutations selected from the group consisting of D70Q, F71Y, I48V and A43S.

In another preferred embodiment of the present invention, provided the humanized LAG-3 antibody or the antigen-binding fragment thereof according to the present invention, wherein the light chain variable region sequence of the humanized antibody is selected from sequence of SEQ ID NO: 22, SEQ ID NO: 26, SEQ ID NO: 27 or SEQ ID NO: 28, or a sequence with at least 85% (preferably 95%) identity to these sequences.

In another preferred embodiment of the present invention, provided the humanized LAG-3 antibody or the antigen-binding fragment thereof according to the present invention, wherein the light chain variable region sequence of the humanized antibody is shown in SEQ ID NO: 30, or a sequence with at least 85% identity to this sequence; preferably there are 0-10 amino acid changes in the light chain variable region; These amino acid changes may be made based on technology of affinity maturation in the art.

In another preferred embodiment of the present invention, provided the humanized LAG-3 antibody or the antigen-binding fragment thereof according to the present invention, wherein the light chain FR sequence of the humanized antibody has 0-10 amino acid back-mutations, preferably has one or more back-mutations selected from the group consisting of L46R, G66R, S60K, P44F, Y36L, K42G I21L and T85D.

In another preferred embodiment of the present invention, provided the humanized LAG-3 antibody or the antigen-binding fragment thereof according to the present invention, wherein the light chain variable region sequence of the humanized antibody is selected from sequence of SEQ ID NO: 30, SEQ ID NO: 34, SEQ ID NO: 35, SEQ ID NO: 36 or SEQ ID NO: 37, or a sequence with at least 85% (preferably 95%) identity to these sequences.

In another preferred embodiment of the present invention, provided the humanized LAG-3 antibody or the antigen-binding fragment thereof according to the present invention, wherein the humanized antibody comprises:

(a) heavy chain variable region sequence, wherein the heavy chain variable region sequence has at least 85% (preferably 95%) identity to the sequence selected from the group consisting of SEQ ID NO: 21, SEQ ID NO: 23, SEQ ID NO: 24 and SEQ ID NO: 25; and (b) light chain variable region sequence, wherein the light chain variable region sequence has at least 85% identity to sequence selected from the group consisting of SEQ ID NO: 22, SEQ ID NO: 26, SEQ ID NO: 27 and SEQ ID NO: 28.

In another preferred embodiment of the present invention, provided the LAG-3 antibody or the antigen-binding fragment thereof according to the present invention, wherein the humanized antibody comprises:

(a) heavy chain variable region sequence, wherein the heavy chain variable region sequence has at least 85% (preferably 95%) identity to the sequence selected from the group consisting of SEQ ID NO: 29, SEQ ID NO: 31, SEQ ID NO: 32 and SEQ ID NO: 33, and (b) light chain variable region sequence, wherein the light chain variable region sequence has at least 85% (preferably 95%) identity to the sequence selected from the group consisting of SEQ ID NO: 30, SEQ ID NO: 34, SEQ ID NO: 35, SEQ ID NO: 36 and SEQ ID NO: 37.

In another preferred embodiment of the present invention, provided the LAG-3 antibody or the antigen-binding fragment thereof according to the present invention, wherein the antibody comprises a combination of a heavy chain variable region and a light chain variable region selected from the group consisting of:

1) the heavy chain variable region of SEQ ID NO: 21 and the light chain variable region of SEQ ID NO: 22;
2) the heavy chain variable region of SEQ ID NO: 21 and the light chain variable region of SEQ ID NO: 26;
3) the heavy chain variable region of SEQ ID NO: 21 and the light chain variable region of SEQ ID NO: 27;
4) the heavy chain variable region of SEQ ID NO: 21 and the light chain variable region of SEQ ID NO: 28;
5) the heavy chain variable region of SEQ ID NO: 23 and the light chain variable region of SEQ ID NO: 22;
6) the heavy chain variable region of SEQ ID NO: 23 and the light chain variable region of SEQ ID NO: 26;
7) the heavy chain variable region of SEQ ID NO: 23 and the light chain variable region of SEQ ID NO: 27;
8) the heavy chain variable region of SEQ ID NO: 23 and the light chain variable region of SEQ ID NO: 28;
9) the heavy chain variable region of SEQ ID NO: 24 and the light chain variable region of SEQ ID NO: 22;
10) the heavy chain variable region of SEQ ID NO: 24 and the light chain variable region of SEQ ID NO: 26;
11) the heavy chain variable region of SEQ ID NO: 24 and the light chain variable region of SEQ ID NO: 27;
12) the heavy chain variable region of SEQ ID NO: 24 and the light chain variable region of SEQ ID NO: 28;
13) the heavy chain variable region of SEQ ID NO: 25 and the light chain variable region of SEQ ID NO: 22;
14) the heavy chain variable region of SEQ ID NO: 25 and the light chain variable region of SEQ ID NO: 26;
15) the heavy chain variable region of SEQ ID NO: 25 and the light chain variable region of SEQ ID NO: 27; and
16) the heavy chain variable region of SEQ ID NO: 25 and the light chain variable region of SEQ ID NO: 28.

In another preferred embodiment of the present invention, provided the LAG-3 antibody or the antigen-binding fragment thereof according to the present invention, wherein the antibody comprises a combination of a heavy chain variable region and a light chain variable region selected from the group consisting of:

1) the heavy chain variable region of SEQ ID NO: 29 and the light chain variable region of SEQ ID NO: 30;

2) the heavy chain variable region of SEQ ID NO: 29 and the light chain variable region of SEQ ID NO: 34;

3) the heavy chain variable region of SEQ ID NO: 29 and the light chain variable region of SEQ ID NO: 35;

4) the heavy chain variable region of SEQ ID NO: 29 and the light chain variable region of SEQ ID NO: 36;

5) the heavy chain variable region of SEQ ID NO: 29 and the light chain variable region of SEQ ID NO: 37;

6) the heavy chain variable region of SEQ ID NO: 31 and the light chain variable region of SEQ ID NO: 30;

7) the heavy chain variable region of SEQ ID NO: 31 and the light chain variable region of SEQ ID NO: 34;

8) the heavy chain variable region of SEQ ID NO: 31 and the light chain variable region of SEQ ID NO: 35;

9) the heavy chain variable region of SEQ ID NO: 31 and the light chain variable region of SEQ ID NO: 36;

10) the heavy chain variable region of SEQ ID NO: 31 and the light chain variable region of SEQ ID NO: 37;

11) the heavy chain variable region of SEQ ID NO: 32 and the light chain variable region of SEQ ID NO: 30;

12) the heavy chain variable region of SEQ ID NO: 32 and the light chain variable region of SEQ ID NO: 34;

13) the heavy chain variable region of SEQ ID NO: 32 and the light chain variable region of SEQ ID NO: 35;

14) the heavy chain variable region of SEQ ID NO: 32 and the light chain variable region of SEQ ID NO: 36;

15) the heavy chain variable region of SEQ ID NO: 32 and the light chain variable region sequence of SEQ ID NO: 37;

16) the heavy chain variable region of SEQ ID NO: 33 and the light chain variable region of SEQ ID NO: 30;

17) the heavy chain variable region of SEQ ID NO: 33 and the light chain variable region of SEQ ID NO: 34;

18) the heavy chain variable region of SEQ ID NO: 33 and the light chain variable region of SEQ ID NO: 35;

19) the heavy chain variable region of SEQ ID NO: 33 and the light chain variable region of SEQ ID NO: 36; and 20) the heavy chain variable region of SEQ ID NO: 33 and the light chain variable region of SEQ ID NO: 37.

In another preferred embodiment of the present invention, provided a chimeric or humanized LAG-3 antibody or the antigen-binding fragment thereof according to the present invention, wherein the heavy chain of the chimeric antibody or the humanized antibody further comprises a heavy chain constant region derived from human IgG1, IgG2, IgG3 or IgG4 or a variant thereof, preferably comprises a heavy chain constant region derived from human IgG4 or a variant thereof, most preferably comprises a heavy chain constant region as shown in SEQ ID NO: 38.

The light chain of said chimeric antibody or said humanized antibody further comprises light chain constant region derived from human κ chain, human λ chain or a variant thereof, most preferably comprises a light chain constant region as shown in SEQ ID NO: 39.

The present invention further provides a pharmaceutical composition which comprises a therapeutically effective amount of the LAG-3 antibody or the antigen-binging fragment thereof described herein and one or more pharmaceutically acceptable carriers, diluents or excipients.

The invention further provides an isolated monoclonal antibody or antigen-binding fragment thereof which competes for binding to LAG-3 with the monoclonal antibody or antigen-binding fragment thereof as described above.

The present invention further provides an isolated nucleic acid encoding the LAG-3 antibody or the antigen-binding fragment described above.

The present invention further provides an expression vector comprising the isolated nucleic acid as described above.

The present invention further provides a host cell transformed with the expression vector as described above, wherein the host cell is selected from the group consisting of prokaryotic cells and eukaryotic cells, preferably eukaryotic cells, more preferably mammalian cells.

The present invention further provides a method for preparing a LAG-3 antibody or the antigen-binding fragment thereof, comprising expressing the antibody or the antigen-binding fragment thereof in the host cell as described above and isolating the antibody or the antigen-binding fragment thereof from the host cell.

The present invention further provides a method for inhibiting the growth of tumor cells in a subject, comprising administering to the subject a therapeutically effective amount of the LAG-3 antibody or the antigen-binding fragment thereof according to the invention, or the pharmaceutical composition comprising the same, thereby inhibiting the tumor growth in the subject.

The present invention further provides use of the above LAG-3 antibody or the antigen-binding fragment thereof, or the pharmaceutical composition containing the same, in the inhibition of tumor cell growth in a subject.

The present invention further provides use of said LAG-3 antibody or the antigen-binding fragment thereof, or the pharmaceutical composition containing the same, in the preparation of a medicament for inhibiting the growth of tumor cells in a subject.

The present invention further provides use of the LAG-3 antibody or the antigen-binding fragment thereof according to the present invention, or the pharmaceutical composition comprising the same, or the nucleic acid described above, in the preparation of a medicament for the treatment of a disease or a condition associated with the involvement of immune cells, wherein the disease or the condition is preferably a cancer. The cancer described herein includes but not limited to ovarian cancer, melanoma (for example, metastatic malignant melanoma), prostate cancer, intestinal cancer (for example, colon and small intestinal cancer), stomach cancer, esophageal cancer, breast cancer, lung cancer, renal cancer (for example, clear cell carcinoma), pancreatic cancer, uterine cancer, liver cancer, bladder cancer, cervical cancer, oral cancer, brain cancer, testicular cancer, skin cancer, thyroid cancer, and hematological malignant tumors including myeloma and chronic/acute leukemia.

DETAILED DESCRIPTION OF THE INVENTION

1. Terms

Figure 1:
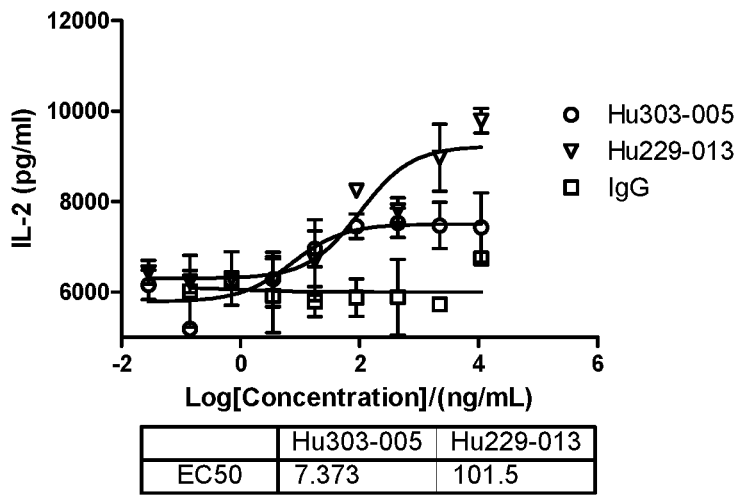
FIG. 1: Humanized anti-LAG-3 antibody enhances secretion of IL-2 cytokine from T lymphocytes activated by SEB. The results show that humanized LAG-3 antibody candidates, Hu229-013 and Hu303-005, can enhance the secretion of cytokine IL-2 from the activated T lymphocytes, and with dose-effect of drug concentration.

In order to more readily understand the invention, certain technical and scientific terms are specifically defined below. Unless specifically defined elsewhere in this document, all other technical and scientific terms used herein have the meaning commonly understood by one of ordinary skill in the art to which this invention belongs.

As used herein, the single-letter code and the three-letter code for amino acids are as described in J. Biol. Chem, 243, (1968) p3558.

The term "LAG-3" refers to Lymphocyte Activation Gene-3. The term "LAG-3" includes variants, isoforms, homologs, orthologs and paralogs. The term "human LAG-3" refers to the sequence of human LAG-3, such as the complete amino acid sequence of human LAG-3 with Uniprot No. P18627. LAG-3 is also known as in the art, for example, CD223. The human LAG-3 sequence may differ from human LAG-3 of Uniprot No. P18627 in that, e.g., the human LAG-3 has conserved mutations or mutations in non-conserved regions and it has substantially the same biological function as the human LAG-3 of Uniprot No. P18627. For example, a biological function of human LAG-3 is an epitope in the extracellular domain of LAG-3 that is specifically bound by the antibody disclosed herein, or a biological function of human LAG-3 is binding to MHC Class II molecules.

A particular human LAG-3 sequence will generally have at least 90% identity in amino acid sequence to human LAG-3 of Uniprot No. P18627 and contains amino acid residues which are identified as being human amino acid sequences when compared to LAG-3 amino acid sequences from other species (e.g., murine). In certain cases, a human LAG-3 can have at least 85%, or even at least 95%, 96%, 97%, 98%, or 99% identity in amino acid sequence to LAG-3 of Uniprot No. P18627. In certain embodiments, a human LAG-3 sequence will display no more than 10 amino acid differences from the LAG-3 sequence of Uniprot No. P18627. In certain embodiments, the human LAG-3 can display no more than 5, or even no more than 4, 3, 2, or 1 amino acid difference from the LAG-3 sequence of Uniprot No. P18627. Percent identity can be determined as described herein.

As used herein, "Sequence identity" indicates the degree of identity between two nucleic acids or two amino acid sequences when optimally aligned and compared in the case of having mutations such as appropriate substitutions, insertions or deletions. The sequence identity between the sequence described in the present invention and the corresponding sequence is at least 85%, 90% or 95%, preferably at least 95%. Representative examples include, but are not limited to, 85%, 86%, 87%, 88%, 89%, 90%, 91%, 92%, 93%, 94%, 95%, 96%, 97%, 98%, 99%, 100%.

The percent identity between two sequences is a function of the number of identical positions shared by the sequences (i.e., % identity=number of identical positions/total number of positions multiplied by 100), taking into account the number of gaps, and the length of each gap, which need to be introduced for optimal alignment of the two sequences. The comparison of sequences and determination of percent identity between two sequences can be accomplished using the default settings of the BLASTN/BLASTP algorithm available on the National Center for Biotechnology Institute's website.

As used herein, "Antibody" refers to immunoglobulin, a four-peptide chain structure connected together by disulfide bonds between two identity heavy chains and two identity light chains. Different immunoglobulin heavy chain constant regions exhibit different amino acid compositions and rank orders, hence present different kinds of antigenicity. Accordingly, immunoglobulins can be divided into five categories, or called as immunoglobulin isotypes, namely IgM, IgD, IgG, IgA and IgE, their heavy chains are µ chain, δ chain, γ chain, α chain and ε chain, respectively. According to its amino acid composition of hinge region and the number and location of heavy chain disulfide bonds, the same type of Ig can be divided into different sub-categories, for example, IgG can be divided into IgG1, IgG2, IgG3, and IgG4. Light chain can be divided into κ or λ chain considering of different constant region. Each of the five types of IgG can have κ or λ chain.

In the present invention, the antibody light chain mentioned herein further comprises a light chain constant region, which comprises a human or murine κ, λ chain or a variant thereof.

In the present invention, the antibody heavy chain mentioned herein further comprises a heavy chain constant region, which comprises human or murine IgG1, IgG 2, IgG 3, IgG 4 or a variant thereof.

Near the N-terminal sequence of the antibody heavy and light chains, about 110 of amino acids change largely, known as variable region (Fv region); the rest of the amino acid sequence near the C-terminus is relative stable, known as constant region. Variable region comprises three hypervariable regions (HVR) and four relatively conserved sequence framework regions (FR). Three hypervariable regions determine the specificity of the antibody, also known as complementarity determining region (CDR). Each light chain variable region (LCVR) and each heavy chain variable region (HCVR) is composed of three CDR regions and four FR regions, with sequential order from the amino terminus to the carboxyl terminus being: FR1, CDR1, FR2, CDR2, FR3, CDR3, and FR4. Three light chain CDRs refer to LCDR1, LCDR2, and LCDR3; three heavy chain CDRs refer to HCDR1, HCDR2 and HCDR3. The number and location of CDR region amino acid residues in LCVR and HCVR regions of the antibody or antigen binding fragment herein comply with known Kabat numbering criteria (LCDR1-3, HCDE2-3), or comply with Kabat and Chothia numbering criteria (HCDR1).

The antibody of the present invention comprises murine antibody, chimeric antibody and humanized antibody, preferable humanized antibody.

The term "murine antibody" in the present invention refers to anti-human LAG-3 monoclonal antibody prepared according to the knowledge and skills of the field. During the preparation, a test subject was injected with LAG-3 antigen, and then hybridoma expressing antibody which possesses desired sequence or functional characteristics was separated. In a preferred embodiment of the present invention, the murine LAG-3 antibody or antigen binding fragment thereof, further comprises light chain constant region of murine κ, λ chain or a variant thereof, or further comprises heavy chain constant region of murine IgG1, IgG2, IgG3, or a variant thereof.

The term "chimeric antibody", is an antibody which is formed by fusing the variable region of a murine antibody with the constant region of a human antibody, the chimeric antibody can alleviate the murine antibody-induced immune response. To establish chimeric antibody, hybridoma secreting specific murine monoclonal antibody is first established, a variable region gene is then cloned from mouse hybridoma cells, then a constant region gene of a human antibody is cloned as desired, the mouse variable region gene is ligated with human constant region gene to form a chimeric gene which can be inserted into a human vector, and finally the chimeric antibody molecule is expressed in the eukaryotic or prokaryotic system. In a preferred embodiment of the present invention, the light chain of LAG-3 chimeric antibody further comprises the light chain constant regions of human κ, λ chain or a variant thereof. The heavy chain of LAG-3 chimeric antibody further comprises the heavy chain constant regions of human IgG1, IgG2, IgG3, IgG4 or a variant thereof, preferably comprises heavy chain constant region of human IgG1, IgG2, IgG3 or IgG4, or preferably comprises heavy chain constant region of human IgG1, IgG2 or IgG4, or a variant thereof with amino acid mutations (e.g., YTE mutations).

The term "humanized antibody", also known as CDR-grafted antibody, refers to an antibody generated by grafting murine CDR sequences into a variable region framework of a human antibody, namely, an antibody produced among different types of human germline antibody framework sequences. Humanized antibody overcomes the heterogenous response induced by the chimeric antibody which carries a large amount of murine protein components. Such framework sequences can be obtained from public DNA database covering germline antibody gene sequences or from published references. For example, germline DNA sequences of human heavy and light chain variable region genes can be found in "VBase" human germline sequence database (available on web www.mrccpe.com.ac.uk/vbase), as well as can be found in Kabat, E A, et al, 1991 Sequences of Proteins of Immunological Interest, 5th Ed. To avoid the decrease in the activity during immunogenicity reduction, the variable region frame sequence of the human antibody is subjected to a minimum back mutation to maintain the activity. The humanized antibody of the present invention also comprises a humanized antibody which is further subjected to CDR affinity maturation by phage display. In a preferred embodiment of the present invention, the murine CDR sequences of the humanized LAG-3 antibody are selected from SEQ ID NOs: 9-20; The variable region frame of human antibody is designed to be selected, wherein the heavy chain FR sequence of the heavy chain variable region of the antibody is derived from the combination sequence of human germline heavy chains IGKV1-39*01 and hjk4.1; wherein the light chain FR sequence of the light chain variable region of the antibody is derived from the combination sequence of human germline heavy chains IGHV3-23*04 and hjh6.1. In order to avoid the decrease of the activity caused by the decrease of immunogenicity, the variable region of the human antibody described herein can be subjected to minimal back-mutations to maintain the activity of antibody.

The grafting of CDRs may result in a decrease in the affinity of the LAG-3 antibody or antigen-binding fragment thereof to the antigen due to the change of framework residues in contact with the antigen. Such interactions may be the result of highly somatic mutations. Thus, it may still be necessary to implant such donor framework amino acids to the framework of humanized antibodies. The amino acid residues involved in antigen binding from nonhuman LAG-3 antibody or antigen-binding fragment thereof can be identified by examining the variable region sequence and structure of murine monoclonal antibody. Each of the residues in the CDR donor framework that is different from the germline may be considered to be relevant. If it is not possible to determine the most closely related species, the sequence can be compared to a consensus sequence of a subtype consensus sequence or a murine sequence with a high similarity percentage. Rare frame residues are thought to be the result of a highly somatic cell mutation, which plays an important role in binding.

The term "antigen-binding fragment" of an antibody (or for short, "antibody fragment"), refers to one or more fragments of an antibody that retain the ability to specifically bind to an antigen (e. g., a LAG-3 protein). It has been shown that the antigen-binding function of an antibody can be performed by a full length antibody fragment. Examples of binding fragments encompassed within the term "antigen binding fragment" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge on the hinge region; (iii) a Fd fragment consisting of the VH and CH1 domains; (iv) a Fv fragment consisting of the VL and VH domains of a single arm of an antibody; (v) a single domain or a dAb fragment (Ward et al., (1989) Nature10 341:544-546), which consists of a VH domain; and (vi) a separate complementarity determining region (CDR) or (vii) optionally a combination of two or more separate CDRs linked by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen binding fragment" of an antibody. These antibody fragments are obtained using conventional techniques known to those with skill in the art, and the fragments are screened for utility in the same manner as for intact antibodies. The antigen-binding moiety can be produced by recombinant DNA techniques or by enzymatic or chemical cleavage of intact immunoglobulins. The antibodies may be antibodies of different isoforms, for example, IgG (e.g., IgG1, IgG2, IgG3 or IgG4 subtype), IgA1, IgA2, IgD, IgE or IgM antibodies.

The term "single chain antibody", "single chain Fv" or "scFv" is intended to refer to a molecule comprising an antibody heavy chain variable domain (or region; VH) and an antibody light chain variable domain (or region; VL) connected by a linker. Such scFv molecules can have the general structures: NH$_2$-VL-linker-VH-COOH or NH$_2$-VH-linker-VL-COOH. A suitable linker in the prior art is composed of a repetitive GGGGS amino acid sequence or a variant thereof, for example a variant with 1-4 repeat (Holliger et al. (1993), Proc. Natl. Acad. Sci. USA90: 6444-6448). Other linkers that may be used in the present invention are described by Alfthan et al., Protein Eng. 8:725-731, Choi et al (2001), Eur. J. Immuno 1.31:94-106, Hu et al. (1996), Cancer Res. 56:3055-3061, Kipriyanov et al. (1999), J. Mol. Biol. 293:41-56 and Roovers et al (2001), Cancer Immunol.

The term "CDR" refers to one of the six hypervariable regions within the variable domains of an antibody that mainly contribute to antigen binding. One of the most commonly used definitions for the six CDRs was provided by Kabat E. A. et al, (1991) Sequences of proteins of immunological interest. NIH Publication 91-3242). As used herein, Kabat's definition of CDRs only applies for CDR1, CDR2 and CDR3 of the light chain variable domain (LCDR1, LCDR 2, LCDR 3, or L1, L2, L3), as well as for CDR2 and CDR3 of the heavy chain variable domain (HCDR2, HCDR3, or H2, H3).

The term "antibody framework", as used herein refers to the part of the variable domain, either VL or VH, which serves as a scaffold for the antigen binding loops (CDRs) of this variable domain. In essence it is the variable domain without the CDRs.

The term "epitope" or "antigenic determinant" refers to a site on an antigen (e.g., particular sites on LAG-3 molecule) to which an immunoglobulin or antibody specifically binds. An epitope typically includes at least 3, 4, 5, 6, 7, 8, 9, 10, 11, 12, 13, 14 or 15 consecutive or non-consecutive amino acids in a unique spatial conformation. See, e.g., Epitope Mapping Protocols in Methods in Molecular Biology, Vol. 66, G E. Morris, Ed. (1996).

The terms "specific binding," "selective binding," "selectively binds," and "specifically binds," refer to binding of an antibody to an epitope on a predetermined antigen. Typically, the antibody binds with an affinity (KD) of approximately less than $10^{-7}$ M, such as approximately less than $10^{-8}$ M, $10^{-9}$ M or $10^{-10}$ M or even lower.

The term "competitive binding" refers to an antibody that recognizes the same epitope (also referred to as an antigenic determinant) or a portion of the same epitope on the extracellular region of human LAG-3 and binds to the antigen as the monoclonal antibody of the present invention. An antibody that binds to the same epitope as the monoclonal antibody of the present invention refers to an antibody that recognizes and binds to the amino acid sequence of human LAG-3 recognized by the monoclonal antibody of the present invention.

The term "KD" of "Kd" refers to the dissociation equilibrium constant of a particular antibody-antigen interaction. Typically, the antibodies of the invention bind to LAG-3 with a dissociation equilibrium constant (KD) of less than approximately $10^{-7}$ M, such as less than approximately $10^{-8}$ M, $10^{-9}$ M or $10^{-10}$ M or even lower, for example, as determined using surface plasmon resonance (SPR) technology in a BIACORE instrument.

The term "nucleic acid molecule" as used herein refers to DNA molecules and RNA molecules. A nucleic acid molecule may be single-stranded or double-stranded, but preferably is double-stranded DNA. A nucleic acid is "effectively linked" when it is placed into a functional relationship with another nucleic acid sequence. For instance, a promoter or enhancer is effectively linked to a coding sequence if it affects the transcription of the sequence.

The term "vector," refers to a nucleic acid molecule capable of transporting another nucleic acid to which it has been linked. In one embodiment, vector is a "plasmid," which refers to a circular double stranded DNA loop into which additional DNA segments may be ligated. In another embodiment, vector is a viral vector, wherein additional DNA segments may be ligated into the viral genome. In present invention, the vectors are capable of autonomous replication in a host cell into which they are introduced (e.g., bacterial vectors having a bacterial origin of replication and episomal mammalian vectors), or can be integrated into the genome of a host cell upon introduction into the host cell, and thereby are replicated along with the host genome (e.g., non-episomal mammalian vectors).

Methods for producing and purifying antibodies and antigen-binding fragments are well known in the art and can be found, for example, in Antibody Experimental Technology Guide of Cold Spring Harbor, Chapters 5-8 and 15. For example, mice can be immunized with human LAG-3, or fragments thereof, and the resulting antibodies can then be re-natured, purified and sequenced by using conventional methods well known in the art. Antigen-binding fragments can also be prepared by conventional methods. The antibody or the antigen-binding fragment of the present invention is genetically engineered to introduce one or more human framework regions (FRs) to a non-human derived CDR. Human FR germline sequences can be obtained from ImMunoGeneTics (IMGT) via their website http://imgt.cines.fr, or from The Immunoglobulin FactsBook, 2001ISBN012441351.

The term "host cell" refers to a cell into which an expression vector has been introduced. Host cells can include bacterial, microbial, plant or animal cells. Bacteria, which are susceptible to be transformed, include members of the enterobacteriaceae, such as strains of *Escherichia coli* or *Salmonella*; Bacillaceae, such as *Bacillus subtilis; Pneumococcus; Streptococcus*, and *Haemophilus influenzae*. Suitable microorganisms include *Saccharomyces cerevisiae* and *Pichia pastoris*. Suitable animal host cell lines include CHO (Chinese Hamster Ovary lines) and NSO cells.

The engineered antibody or antigen-binding fragment of the present invention may be prepared and purified using conventional methods. For example, cDNA sequences encoding a heavy chain and a light chain may be cloned and recombined into a GS expression vector. The recombinant immunoglobulin expression vector may then stably transfect CHO cells. As a more recommended method well known in the art, mammalian expression system will result in glycosylation, typically at the highly conserved N-terminus in the FC region. Stable clones are obtained through expression of an antibody specifically binding to human LAG-3. Positive clones may be expanded in a serum-free culture medium for antibody production in bioreactors. Culture medium, into which an antibody has been secreted, may be purified by conventional techniques. For example, the medium may be conveniently applied to a Protein A or G Sepharose FF column that has been equilibrated with a compatible buffer. The column is washed to remove nonspecific binding components. The bound antibody is eluted by PH gradient and antibody fragments are detected by SDS-PAGE, and then pooled. The antibody may be filtered and concentrated using common techniques. Soluble mixture and aggregate may be effectively removed by common techniques, including size exclusion or ion exchange. The obtained product may be immediately frozen, for example at −70° C., or may be lyophilized.

"Administration" and "treatment," as it applies to an animal, human, experimental subject, cell, tissue, organ, or biological fluid, refers to contacting an exogenous pharmaceutical, therapeutic, diagnostic agent, or composition with the animal, human, subject, cell, tissue, organ, or biological fluid. "Administration" and "treatment" can refer, e.g., to therapeutic, pharmacokinetic, diagnostic, research, and experimental methods. Treatment of a cell encompasses contacting a reagent with the cell, as well as contacting a reagent with a fluid, where the fluid is in contact with the cell. "Administration" and "treatment" also means in vitro and ex vivo treatments, e.g., of a cell, by a reagent, diagnostic, binding compound, or by another cell. "Treatment," as it applies to a human, veterinary, or a subject to be studied, refers to therapeutic treatment, prophylactic or preventative measures, to research and diagnostic applications.

"Treat" means to administer a therapeutic agent, such as a composition comprising any of the binding compounds of the present invention, internally or externally to a patient having one or more disease symptoms for which the agent has known therapeutic activity. Typically, the agent is administered in an amount effective to alleviate one or more disease symptoms in the treated patient or population, whether by inducing the regression of or inhibiting the progression of such symptom(s) to any clinically measurable degree. The amount of a therapeutic agent that is effective to alleviate any particular disease symptom (also referred to "therapeutically effective amount") may vary according to factors such as the disease state, age, and weight of the patient, and the ability of the drug to elicit a desired response in the patient. Whether a disease symptom has been alleviated can be assessed by any clinical measurement typically used by physicians or other skilled healthcare providers to assess the severity or progression status of that symptom. While an embodiment of the present invention (e.g., a treatment method or article of manufacture) may not be effective in alleviating the disease symptom(s) of interest in every patient, it should alleviate the target disease symptom(s) of interest in a statistically significant number of patients as determined by any statistical test known in the art such as the Student's t-test, the chi-square test, the U-test according to Mann and Whitney, the Kruskal-Wallis test (H-test), Jonckheere-Terpstra-test and the Wilcoxon-test.

"Conservative modifications" or "conservative replacement or substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein. Those of skill in this art recognize that, in general, single amino acid substitutions in non-essential regions of a polypeptide do not substantially alter biological activity (see, e.g., Watson et al. (1987) Molecular Biology of the Gene, The Benjamin/Cummings Pub. Co., p. 224 (4.sup.th Ed.)). In addition, substitutions with structurally or functionally similar amino acids are less likely to disrupt biological activity.

"Effective amount" encompasses an amount sufficient to ameliorate or prevent a symptom or sign of a medical condition. Effective amount also means an amount sufficient to allow or facilitate diagnosis. An effective amount for a particular patient or veterinary subject may vary depending on factors such as the condition being treated, the general health of the patient, the route and dose of administration and the severity of side effects. An effective amount can be the maximal dose or dosing protocol that avoids significant side effects or toxic effects.

"Exogenous" refers to substances that are produced outside an organism, cell, or human body, depending on the context. "Endogenous" refers to substances that are produced within a cell, organism, or human body, depending on the context.

"Homology" refers to sequence similarity between two polynucleotide sequences or between two polypeptides. When a position in both of the two sequences to be compared is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared multiplying by 100. For example, if 6 of 10 positions in two sequences are matched or homologous when the sequences are optimally aligned, then the two sequences are 60% homologous. If 95 of 100 positions in two sequences are matched or homologous when the sequences are optimally aligned, then the two sequences are 95% homologous. Generally, the comparison is made when two sequences are aligned to give maximum percent homology.

As used herein, the expressions "cell," "cell line," and "cell culture" are used interchangeably and all such designations include progeny. Thus, the words "transformants" and "transformed cells" include the primary subject cell and cultures derived therefrom without considering the number of transfers. It is also understood that all progeny may not be precisely identity in DNA content, due to deliberate or inadvertent mutations. Mutant progeny that have the same function or biological activity as screened for in the originally transformed cell are included. Where distinct designations are intended, it will be clear from the context.

As used herein, "polymerase chain reaction" or "PCR" refers to a procedure or technique in which minute amounts of a specific moiety of nucleic acid, RNA and/or DNA, are amplified as described in, e.g., U.S. Pat. No. 4,683,195. Generally, sequence information from the ends of, or beyond the region of interest needs to be available, such that oligonucleotide primers can be designed; these primers will be identical or similar in sequence to the corresponding strands of the template to be amplified. The 5' terminal nucleotides of the two primers can be identical to the ends of the material to be amplified. PCR can be used to amplify specific RNA sequences, specific DNA sequences from total genomic DNA, and cDNA transcribed from total cellular RNA, bacteriophage or plasmid sequences, etc. See generally Mullis et al. (1987) Cold Spring Harbor Symp. Ouant. Biol. 51:263; Erlich, ed., (1989) PCR TECHNOLOGY (Stockton Press, N.Y.). As used herein, PCR is considered as one, but not the only, example of a nucleic acid polymerase reaction method for amplifying a nucleic acid test sample, comprising the use of a known nucleic acid as a primer and a nucleic acid polymerase to amplify or generate a specific moiety of the nucleic acid.

"Optional" or "optionally" means that the event or situation that follows may but does not necessarily occur, and the description includes the instances in which the event or circumstance does or does not occur. For example, "optionally comprises 1-3 antibody heavy chain variable regions" means the antibody heavy chain variable region with specific sequence can be, but not necessarily be present.

"Pharmaceutical composition" refers to a mixture containing one or more compounds according to the present invention or a physiologically/pharmaceutically acceptable salt or prodrug thereof and other chemical components, such as physiologically/pharmaceutically acceptable carriers and excipients. The pharmaceutical composition aims at promoting the administration to an organism, facilitating the absorption of the active ingredient and thereby exerting a biological effect.

EXAMPLE AND TEST

Hereinafter, the present invention is further described with reference to the examples. However, the scope of the present invention is not limited thereto. In the examples of the present invention, where specific conditions are not described, the experiments are generally conducted under conventional conditions as described in Antibody Technology Laboratory Manual and Molecular Cloning Manual of Cold Spring Harbor, or under conditions proposed by the material or product manufacturers. Where the source of the reagents is not specifically given, the reagents are commercially available conventional reagents.

Example 1

Preparation of LAG-3 Antigen and Antibody

1. Protein Design and Expression

UniProt Lymphocyte activation gene 3 protein (human LAG-3, Uniprot: P18627) was used as the template of the LAG-3, and the amino acid sequences of the antigen and the protein used for detection were designed, optionally different labels were fused to the LAG-3 protein and then cloned into pHr vector (produced in-house) or pTT5 vector (Biovector, Cat #: 102762) or pTargeT vector (Promega, A1410). The antigen protein and the detection protein of the present invention were transiently expressed in 293 cells or stably expressed in CHO-S, purified and obtained.

The following LAG-3 antigens are referred to human LAG-3 if not specifically described.

LAG-3 Extracellular domain with a Flag tag: LAG-3-Flag, for immunization of mice.

SEQ ID NO: 1
<u>MWEAQFLGLLFLQPLWVAPVKP</u>LQPGAEVPVVWAQEGAPAQLPCSPTI
PLQDLSLLRRAGVTWQHQPDSGPPAAAPGHPLAPGPHPAAPSSWGPRP
RRYTVLSVGPGGLRSGRLPLQPRVQLDERGRQRGDFSLWLRPARRADA
GEYRAAVHLRDRALSCRLRLRLGQASMTASPPGSLRASDWVILNCSFS
RPDRPASVHWFRNRGQGRVPVRESPHHHLAESFLFLPQVSPMDSGPWG
CILTYRDGFNVSIMYNLTVLGLEPPTPLTVYAGAGSRVGLPCRLPAGV
TRSFLTAKWTPPGGGPDLLVTGDNGDFTLRLEDVSQAQAGTYTCHIHL
QEQQLNATVTLAIITVTPKSFGSPGSLGKLLCEVTPVSGQERFVWSSL
DTPSQRSFSGPWLEAQEAQLLSQPWQCQLYQGERLLGAAVYFTELSSP
*GDYKDDDDK*

NOTE: Underlined sequence represents a signal peptide, and italic part refers to the Flag-tag sequence.

The full length sequence of LAG-3: Used to construct LAG-3 overexpressing cell line, for immunization of mice and detection SEQ ID NO: 2
<u>MWEAQFLGLLFLQPLWVAPVKP</u>LQPGAEVPVVWAQEGAPAQLPCSPTI
PLQDLSLLRRAGVTWQHQPDSGPPAAAPGHPLAPGPHPAAPSSWGPRP
RRYTVLSVGPGGLRSGRLPLQPRVQLDERGRQRGDFSLWLRPARRADA
GEYRAAVHLRDRALSCRLRLRLGQASMTASPPGSLRASDWVILNCSFS
RPDRPASVHWFRNRGQGRVPVRESPHHHLAESFLFLPQVSPMDSGPWG
CILTYRDGFNVSIMYNLTVLGLEPPTPLTVYAGAGSRVGLPCRLPAGV
GTRSFLTAKWTPPGGGPDLLVTGDNGDFTLRLEDVSQAQAGTYTCHIH
LQEQQLNATVTLAIITVTPKSFGSPGSLGKLLCEVTPVSGQERFVWSS
LDTPSQRSFSGPWLEAQEAQLLSQPWQCQLYQGERLLGAAVYFTELSS
PGAQRSGRAPGALPAGH<u>LLLFLILGVLSLLLLVTGAFGF</u>HLWRRQWRP
*RRFSALEQGIHPPQAQSKIEELEQEPEPEPEPEPEPEPEPEPEPEQL*

NOTE: Signal peptide+extracellular domain+transmembrane region+intracellular domain A fusion protein of LAG-3 extracellular domain and hIgG1 Fc: LAG-3-Fc, for detection SEQ ID NO: 3
<u>MWEAQFLGLLFLQPLWVAPVKP</u>LQPGAEVPVVWAQEGAPAQLPCSPTI
PLQDLSLLRRAGVTWQHQPDSGPPAAAPGHPLAPGPHPAAPSSWGPRP
RRYTVLSVGPGGLRSGRLPLQPRVQLDERGRQRGDFSLWLRPARRADA
GEYRAAVHLRDRALSCRLRLRLGQASMTASPPGSLRASDWVILNCSFS
RPDRPASVHWFRNRGQGRVPVRESPHHHLAESFLFLPQVSPMDSGPWG
CILTYRDGFNVSIMYNLTVLGLEPPTPLTVYAGAGSRVGLPCRLPAGV
GTRSFLTAKWTPPGGGPDLLVTGDNGDFTLRLEDVSQAQAGTYTCHIH
LQEQQLNATVTLAIITVTPKSFGSPGSLGKLLCEVTPVSGQERFVWSS
LDTPSQRSFSGPWLEAQEAQLLSQPWQCQLYQGERLLGAAVYFTELSS
PG<u>DDDDKGSGSG</u>*EPKSCDKTHTCPPCPAPELLGGPSVFLFPPKPKDTL*
*MISRTPEVTCVVVDVSHEDPEVKFNWYVDGVEVHNAKTKPREEQYNST*
*YRVVSVLTVLHQDWLNGKEYKCKVSNKALPAPIEKTISKAKGQPREPQ*
*VYTLPPSREEMTKNQVSLTCLVKGFYPSDIAVEWESNGQPENNYKTTP*
*PVLDSDGSFFLYSKLTVDKSRWQQGNVFSCSVMHEALHNHYTQKSLSL*
*SPG*

NOTE: Underlined sequence represents a signal peptide, double underlined sequence represents a linker, and the italic part represents Fc.

A fusion protein of LAG-3 extracellular domain and mIgG2a Fc:

LAG-3-mFc, for detection

SEQ ID NO: 4
<u>MWEAQFLGLLFLQPLWVAPVKP</u>LQPGAEVPVVWAQEGAPAQLPCSPTI
PLQDLSLLRRAGVTWQHQPDSGPPAAAPGHPLAPGPHPAAPSSWGPRP
RRYTVLSVGPGGLRSGRLPLQPRVQLDERGRQRGDFSLWLRPARRADA
GEYRAAVHLRDRALSCRLRLRLGQASMTASPPGSLRASDWVILNCSFS
RPDRPASVHWFRNRGQGRVPVRESPHHHLAESFLFLPQVSPMDSGPWG
CILTYRDGFNVSIMYNLTVLGLEPPTPLTVYAGAGSRVGLPCRLPAGV
GTRSFLTAKWTPPGGGPDLLVTGDNGDFTLRLEDVSQAQAGTYTCHIH
LQEQQLNATVTLAIITVTPKSFGSPGSLGKLLCEVTPVSGQERFVWSS
LDTPSQRSFSGPWLEAQEAQLLSQPWQCQLYQGERLLGAAVYFTELSS
PG<u>DDDDKGSGSG</u>*EPRGPTIKPCPPCKCPAPNLLGGPSVFIFPPKIKDV*
*LMISLSPIVTCVVVDVSEDDPDVQISWFVNNVEVHTAQTQTHREDYNS*
*TLRVVSALPIQHQDWMSGKEFKCKVNNKDLPAPIERTISKPKGSVRAP*
*QVYVLPPPEEEMTKKQVTLTCMVTDFMPEDIYVEWTNNGKTELNYKNT*
*EPVLDSDGSYFMYSKLRVEKKNWVERNSYSCSVVHEGLHNHHTTKSFS*
*RTPGK*

NOTE: Underlined sequence represents a signal peptide, double underlined sequence represents a linker, and the italic part represents Fc.

2. Purification of LAG-3-Related Recombinant Protein, as Well as Hybridoma Antibody, and Recombinant Antibody 1. Purification Steps for LAG-3-Flag Recombinant Protein with a Flag Tag The sample was centrifuged at high speed to remove impurities and concentrated to an appropriate volume. After that, the flag affinity column was equilibrated with 0.5×PBS and washed with 2-5 column volumes. The supernatant samples were loaded on the column after removing the impurity. Washing the column with 0.5×PBS until the A280 reading was reduced to baseline. Then, the column was washed with PBS, and the impurity protein was washed off and then collected. The target protein was eluted with 100 mM glycine, pH 3.0 and collected for further activation and purification in vitro.

2. Purification Steps for Hybridoma Antibody, Recombinant Antibody and Fc Fusion Protein The cell-expressing supernatant was centrifuged at high speed to remove impurities, hybridoma expressing supernatant was purified by Protein G column, recombinant antibody and Fc fusion protein were purified by Protein A column. Washing the column with 0.5×PBS until the A280 reading was reduced to baseline. After that, the target protein was eluted with 100 mM acetic acid (pH 3.0) and neutralized with 1 M Tris-HCl, pH 8.0. The eluted sample was properly concentrated and further purified using gel chromatography Superdex200 (GE), which was equilibrated with PBS, the mismatch peak was excluded and the correct sample was aliquoted for use.

Example 2

Preparation of Anti-Human LAG-3 Monoclonal Antibody

1. Immunization

The anti-human LAG-3 monoclonal antibody was produced by immunizing mice. Experimental SJL white mice, female, 6-week old (Beijing Weitong Lihua Experimental Animal Technology Co., Ltd., animal production license number: SCXK (Beijing) 2012-0001). Feeding environment: SPF level. After the mice were purchased, the animals were kept in the laboratory for 1 week, with 12/12-hour light/dark cycle, at temperature of 20-25° C., and with a humidity of 40-60%. The mice that had been adapted to the environment were immunized according to the following schemes. Immune antigen was extracellular domain of LAG-3 with Flag tag (SEQ ID NO: 1).

Scheme A: Mice were cross-immunized with TiterMax® Gold Adjuvant (sigma Lot Num: T2684) and Thermo Imject® Alum (Thremo Lot Num: 77161). The ratio of antigen to adjuvant (TiterMax® Gold Adjuvant) was 1:1, and the ratio of antigen to adjuvant (Thermo Imject® Alum) was 3:1, with a dose of 50 µg/mouse (first immunization) and 25 µg/mouse (booster immunization). After the antigen was emulsified, the mice were inoculated on day 0, 7, 14, 21, 28, 35 and 42. On day 0, the mice were, on several locations, subcutaneously (s.c.) injected with emulsified antigen, 50 µg/mouse. On day 7, the mice were intraperitoneally (i.p.) injected with 25 µg/mouse. On days 14, 28, 35 and 42, either back or intraperitoneal injection of antigen was selected according to the lumps on the back and the swelling conditions in abdomen. Blood samples were collected on days 21, 35, 49, and antibody titers in mouse serum were determined by ELISA. After 7 immunizations, mice with higher antibody titer and the titer tending to platform in their serum were selected for splenocyte fusion, a booster immunization was performed by i.p. injection of antigen solution formulated with saline, 50 µg/mouse, 3 days prior to splenocyte fusion.

Scheme B: Mice were immunized with QuickAntibody-Mouse5W (KX0210041). The ratio of antigen to adjuvant was 1:1, 25 µg/mouse (first immunization/booster immunization). The antigen and adjuvant were rapidly mixed and used for inoculation. Mice were inoculated on days 0, 21 and 35. On day 0, the mouse was injected with antigens via posterior calf muscles (i.m.), 25 µg/mouse, On days 21 and 35, the same way of injection was repeated, 25 µg/mouse, (whether the third immunization was performed or not is dependent on the antibody titer). Blood samples were collected on days 28 and 42. The antibody titer in mouse serum was determined by ELISA. Mice with higher antibody titer and the titer tending to platform in their serum were selected for splenocyte fusion, a booster immunization was performed by i.p. injection of antigen solution formulated with saline, 50 µg/mouse, 3 days prior to splenocyte fusion.

2. Splenocyte Fusion

Hybridoma cells were obtained by fusing splenic lymphocyte with myeloma Sp2/0 cells (ATCC® CRL-8287™) by using an optimized PEG-mediated fusion procedure. The hybridoma cells obtained were resuspended in a complete medium (DMEM medium containing 20% FBS, 1×HAT and 1×OPI) at a density of $0.5-1\times10^6$/ml, and incubated in 96-well cell culture plates, 100 µl/well. After incubation at 37° C., 5% $CO_2$, for 3-4 days, 100 µl/well of the HAT complete medium was supplemented and the culture was continued for 3-4 days to form a needle-like clone. The supernatant was removed and 200 µl/well of HT complete medium (RPMI-1640 medium containing 20% FBS, 1×HAT, 1×OPI) was added, cultured at 5% $CO_2$, 37° C. for three days and then detected by ELISA assay.

3. Screening for Hybridoma Cells

Hybridoma culture supernatant was detected by binding ELISA (see Test Example 1) according to the growth density of hybridoma cells. And cell-blocking experiments were performed with positive wells of ELISA (see Test Example 3). Cells which were positive both for binding and blocking experiments were expanded and frozen stored in timely, and the cells were subcloned twice to three times until single cell clone was obtained.

After each subcloning procedure, the cells were subjected to LAG-3 binding ELISA and cell blocking assay (see Test Example 1 and Test Example 3). The hybridoma clones were obtained by the above screening experiments, and the antibody was further prepared by serum-free cell culture method, and then the antibody was purified according to purification example for use in the test example.

4. Sequencing of the Positive Hybridoma Clone

The process of cloning sequence from the positive hybridoma was as follows: Collecting the hybridoma cells at logarithmic growth phase, and extracting RNA with Trizol (Invitrogen Cat, No. 15596-018) according to the kit instructions, and then performing reverse transcription with the PrimeScript™ Reverse Transcriptase kit (Takara, Cat No. 2680A). The cDNAs obtained by reverse transcription were amplified by PCR using the mouse Ig-Primer Set (Novagen, TB326 Rev. B 0503) and sequencing was performed in a sequencing company. The heavy chain and light chain amino acid sequences corresponding to DNA sequences of hybridoma clone mAb229 and mAb303 are shown in SEQ ID NOs: 5, 6 and SEQ ID NOs: 7, 8, respectively.

mAb229-VH
SEQ ID NO: 5
QIQLVQSGPELKKPGETVKISCKASGYTFT<u>TSGMS</u>WVKQAPGKGLKWM
G<u>WINTYSGVPTYADDFKG</u>RFAFSLETSASTAYLQINNLKNEDTATYFC
AR<u>DNYDARDVYYYAMDY</u>WGQGTSVTVSS mAb229-VL
SEQ ID NO: 6
DIQMTQSPASLSVSVGETVTITC<u>RASENIYSNLA</u>WYQQKQGKSPQLLV
Y<u>AATNLAD</u>GVPSRFSGSGSGTQYSLKINSLQSEDFGSYYC<u>QHFWITPW</u>
TFGGGTKLEIK mAb303-VH
SEQ ID NO: 7
EVQLQQSGPVLVKPGASVKMSCKASGYTLT<u>DYYMN</u>WVKQSHGKSLEWI
G<u>VINPYNGDTAYNQKFKG</u>KATLTVDKSSNTAYMEINSLTSEDSAVYYC
TR<u>DDGYYDYYFDV</u>WGTGTTVTVSS mAb303-VL
SEQ ID NO: 8
DIQMTQSPSSLSASLGERVILTC<u>RASQDIGSRLN</u>WLQQGPDGTFKRLI
Y<u>ATSTLDS</u>GVPKRFSGSRSGSDFSLTISSLESEDFVDYYC<u>LQLASSPP</u>
TFGGGTKLEIK

TABLE 1

CDR region sequences of heavy chain and light chain

| | Heavy chain | Light chain |
|---|---|---|
| mAb229 | HCDR1 TSGMS<br>SEQ ID NO: 9<br>HCDR2 WINTYSGVPTYADDFKG<br>SEQ ID NO: 10<br>HCDR3 DNYDARDVYYYAMDY<br>SEQ ID NO: 11 | LCDR1 RASENIYSNLA<br>SEQ ID NO: 15<br>LCDR2 AATNLAD<br>SEQ ID NO: 16<br>LCDR3 QHFWITPWT<br>SEQ ID NO: 17 |
| mAb303 | HCDR1 DYYMN<br>SEQ ID NO: 12<br>HCDR2 VINPYNGDTAYNQKFKG<br>SEQ ID NO: 13<br>HCDR3 DDGYYDYYFDV<br>SEQ ID NO: 14 | LCDR1 RASQDIGSRLN<br>SEQ ID NO: 18<br>LCDR2 ATSTLDS<br>SEQ ID NO: 19<br>LCDR3 LQLASSPPT<br>SEQ ID NO: 20 |

The obtained positive clones were subjected to an ELISA assay of binding to human LAG-3 (Test Example 1, the results of EC50 value for the protein binding activity are shown in Table 2), ELISA assay of binding to human LAG-3 overexpressing CHO-s cells (Test Example 2, the results of EC50 values for the cell binding activity are shown in Table 2), and an assay for blocking the binding of LAG-3 antigen to Daudi cells (Test Example 3, the results of EC50 value for blocking activity are shown in Table 2), and assay for its affinity with human LAG-3 protein (see Test Example 4, results are shown in Table 3).

TABLE 2

In vitro Activity of Murine LAG-3 Antibody

| Candidate antibody | Protein binding activity EC50(nM) | Cell binding activity EC50(nM) | Blocking activity IC50 (nM) |
|---|---|---|---|
| mAb229 | 0.129 | 0.191 | 1.327 |
| mAb303 | 0.172 | 0.279 | 0.596 |

TABLE 3

Affinity of Murine LAG-3 antibody

| Stationary phase | Mobile phase | Affinity(M) |
|---|---|---|
| mAb229 | LAG-3-Flag | 4.26E−10 |
| mAb303 | | 4.70E−10 |

The results shown in table 2 demonstrate that both the LAG-3 antibody mAb229 and mAb303 showed excellent binding activity to human LAG-3 protein and the two also showed excellent binding activity to CHO-S cells overexpressing full-length of human LAG-3 protein. Both LAG-3 antibody mAb229 and mAb303 significantly blocked the binding of human LAG-3 antigen with Daudi cells.

The results shown in table 3 demonstrate that the LAG-3 antibody mAb229 and mAb303 of the present invention showed a stronger binding activity and affinity to human LAG-3 protein.

Example 3. Humanization of Murine Anti-Human LAG-3 Hybridoma Monoclonal Antibody mAb229

Through comparison in the IMGT human antibody heavy and light chain variable region gene database and MOE software, the heavy and light chain variable region germline genes with high homology to mAb229 were selected as templates, the CDRs derived from murine antibodies were grafted into the corresponding human source template to form a variable region sequence with the order in FR1-CDR1-FR2-CDR2-FR3-CDR3-FR4. Wherein, amino acid residues were identified and annotated according to Kabat Numbering System.

1. Selection of a Framework for Humanizing Hybridoma Clone mAb229

The light chain template for humanizing murine antibody mAb229 is IGKV1-39*01 and hjk4.1, the heavy chain template for humanization is IGHV7-4-1*01 and hjh6.1, the sequences of humanized variable region are as follows:

Hu229VH-CDR graft
SEQ ID NO: 21
*QVQLVQSGSELKKPGASVKVSCKASGYTFT*<u>TSGMS</u>*WVRQAPGQGLEWM
G*<u>WINTYSGVPTYADDFKG</u>*RFVFSLDTSVSTAYLQISSLKAEDTAVYYC
AR*<u>DNYDARDVYYYAMDY</u>*WGQGTTVTVSS*

Hu229VL-CDR graft
SEQ ID NO: 22
*DIQMTQSPSSLSASVGDRVTITC*<u>RASENIYSNLA</u>*WYQQKPGKAPKLLI
Y*<u>AATNLAD</u>*GVPSRFSGSGSGTDFTLTISSLQPEDFATYYC*<u>QHFWITPW</u>
TFGGGTKVEIK NOTE: The order is FR1-CDR1-FR2-CDR2-FR3-CDR3-FR4, italic sequence represents FR sequence, and underlined sequence represents CDR sequence.

2. Template Selection and Back-Mutation Design for Hybridoma Clone mAb229, see Table 4 below

| Hu229_VL | | Hu229_VH | |
|---|---|---|---|
| Hu229_VL.1 | Grafted | Hu229_VH.1 | Grafted |
| Hu229_VL.1A | I48V, F71Y | Hu229_VH.1A | E46K |
| Hu229_VL.1B | D70Q, F71Y, I48V | Hu229_VH.1B | E46K, R38K, V93T |

-continued

| Hu229_VL | | Hu229_VH | |
|---|---|---|---|
| Hu229_VL.1C | D70Q, F71Y, I48V, A43S | Hu229_VH.1C | E46K, R38K, V93T, Y95F |

NOTE:
For example, I48V denotes a back mutation from I to V at position 48 according to Kabat numbering system. Grafted indicates that the murine antibody CDR was implanted into human germline FR sequences.

TABLE 5

Sequence combinations for humanizing murine antibody mAb229

|  | Hu229_VL.1 | Hu229_VL.1A | Hu229_VL.1B | Hu229_VL.1C |
|---|---|---|---|---|
| Hu229_VH.1 | Hu229-004 | LF 229-005 | Hu229-006 | Hu229-007 |
| Hu229_VH.1A | Hu229-008 | Hu229-009 | Hu229-010 | Hu229-011 |
| Hu229_VH.1B | Hu229-012 | Hu229-013 | Hu229-014 | Hu229-015 |
| Hu229_VH.1C | Hu229-016 | Hu229-017 | Hu229-018 | Hu229-019 |

NOTE:
This table shows various sequence combinations of different mutations. For example, Hu229-005 indicates that two mutations (light chain HumAb229_VL.1A and heavy chain HumAb229_VH.1) are present in the humanized murine antibody Hu229-005, and so on.

Sequences of humanized antibody mAb229 are as follows:

Hu229VH.1 (identical to Hu229VH-CDR graft)
SEQ ID NO: 21
QVQLVQSGSELKKPGASVKVSCKASGYTFTTSGMSWVRQAPGQGLEWMGW
INTYSGVPTYADDFKGRFVFSLDTSVSTAYLQISSLKAEDTAVYYCARDN
YDARDVYYYAMDYWGQGTTVTVSS Hu229VH.1A
SEQ ID NO: 23
QVQLVQSGSELKKPGASVKVSCKASGYTFTTSGMSWVRQAPGQGLKWMGW
INTYSGVPTYADDFKGRFVFSLDTSVSTAYLQISSLKAEDTAVYYCARDN
YDARDVYYYAMDYWGQGTTVTVSS Hu229VH.1B
SEQ ID NO: 24
QVQLVQSGSELKKPGASVKVSCKASGYTFTTSGMSWVKQAPGQGLKWMGW
INTYSGVPTYADDFKGRFVFSLDTSVSTAYLQISSLKAEDTATYYCARDN
YDARDVYYYAMDYWGQGTTVTVSS Hu229VH.1C
SEQ ID NO: 25
QVQLVQSGSELKKPGASVKVSCKASGYTFTTSGMSWVRQAPGQGLKWMGW
INTYSGVPTYADDFKGRFVFSLDTSVSTAYLQISSLKAEDTATYFCARDN
YDARDVYYYAMDYWGQGTTVTVSS Hu229VL.1 (identical to Hu229VL-CDR graft)
SEQ ID NO: 22
DIQMTQSPSSLSASVGDRVTITCRASENIYSNLAWYQQKPGKAPKLLIYA
ATNLADGVPSRFSGSGSGTDFTLTISSLQPEDFATYYCQHFWITPWTFGG
GTKVEIK Hu229VL.1A
SEQ ID NO: 26
DIQMTQSPSSLSASVGDRVTITCRASENIYSNLAWYQQKPGKAPKLLVYA
ATNLADGVPSRFSGSGSGTDYTLTISSLQPEDFATYYCQHFWITPWTFGG
GTKVEIK Hu229VL.1B
SEQ ID NO: 27
DIQMTQSPSSLSASVGDRVTITCRASENIYSNLAWYQQKPGKAPKLLVYA
ATNLADGVPSRFSGSGSGTQYTLTISSLQPEDFATYYCQHFWITPWTFGG
GTKVEIK Hu229VL.1C
SEQ ID NO: 28
DIQMTQSPSSLSASVGDRVTITCRASENIYSNLAWYQQKPGKSPKLLVYA
ATNLADGVPSRFSGSGSGTQYTLTISSLQPEDFATYYCQHFWITPWTFGG
GTKVEIK Example 4. Humanization of Murine Anti-Human LAG-3 Hybridoma Monoclonal Antibody mAb303

Through comparison in the IMGT human antibody heavy and light chain variable region gene database and MOE software, the heavy and light chain variable region germline genes with high homology to mAb303 were selected as templates, the CDRs derived from murine antibodies were grafted into the corresponding human source template to form a variable region sequence with the order in FR1-CDR1-FR2-CDR2-FR3-CDR3-FR4. Wherein, amino acid residues were identified and annotated according to the Kabat Numbering System.

1. Selection of a Framework for Humanizing Hybridoma Clone mAb303

The light chain template for humanizing murine antibody mAb303 is IGKV1-39*01 and hjk4.1, the heavy chain template for humanization is IGHV1-3*01 and hjh6.1, the sequences of humanized variable region are as follows:

Hu303VH-CDR graft
SEQ ID NO: 29
*QVQLVQSGAEVKKPGASVKVSCKASGYTFT*DYYMN*WVRQAPGQRLEWM*
*G*VINPYNGDTAYNQKFKG*RVTITRDTSASTAYMELSSLRSEDTAVYYC*
AR DDGYYDYYFDV *WGQGTTVTVSS*

Hu303VL-CDR graft
SEQ ID NO: 30
*DIQMTQSPSSLSASVGDRVTITC*RASQDIGSRLN*WYQQKPGKAPKLLI*
*YA*TSTLDS*GVPSRFSGSGSGTDFTLTISSLQPEDFATYYC*LQLASSPP
T*FGGGTKVEIK*

NOTE: The order is FR1-CDR1-FR2-CDR2-FR3-CDR3-FR4, italic sequence represents FR sequence, and the underlined sequence represents CDR sequence.

2. Template Selection and Back-Mutation Design of Hybridoma Clone mAb303, See Table 6 Below

| Hu303_VL | | Hu303_VH | |
|---|---|---|---|
| Hu303_VL.1 | Grafted | Hu303_VH.1 | Grafted |
| Hu303_VL.1A | L46R, G66R | Hu303_VH.1A | R72V, T74K, A97T |
| Hu303_VL.1B | L46R, G66R, S60K | Hu303_VH.1B | R72V, T74K, A97T, F29L |
| Hu303_VL.1C | L46R, G66R, S60K, P44F, Y36L | Hu303_VH.1C | R72V, T74K, F29L, A97T, M48I, V68A, I70L |
| Hu303_VL.1D | L46R, G66R, S60K, P44F, Y36L, K42G, I21L, T85D | | |

NOTE:
For example, L46R denotes a back mutation from L to R at position 46 according to Kabat numbering system. Grafted indicates that the murine antibody CDR was implanted into human germline FR sequences.

Sequence combinations of different mutations are as follows:

TABLE 7

Sequence combinations for humanization of murine antibody mAb303

| | Hu303_VL.1 | Hu303_VL.1A | Hu303_VL.1B | Hu303_VL.1C | Hu303_VL.1D |
|---|---|---|---|---|---|
| Hu303_VH.1 | Hu303-004 | Hu303-005 | Hu303-006 | Hu303-007 | Hu303-008 |
| Hu303_VH.1A | Hu303-009 | Hu303-010 | Hu303-011 | Hu303-012 | Hu303-013 |
| Hu303_VH.1B | Hu303-014 | Hu303-015 | Hu303-016 | Hu303-017 | Hu303-018 |
| Hu303_VH.1C | Hu303-019 | Hu303-020 | Hu303-021 | Hu303-022 | Hu303-023 |

NOTE:
This table shows various sequence combinations of different mutations. For example, Hu303-005 indicates that two mutations (light chain HumAb303_VL.1A and heavy chain HumAb303_VH.1) are present on the humanized murine antibody Hu303-005, and so on.

Sequences of humanized antibody mAb303 are as follows:

Hu303_VH.1 (identical to Hu303VH-CDR graf)
SEQ ID NO: 29
QVQLVQSGAEVKKPGASVKVSCKASGYTFTDYYMNWVRQAPGQRLEWMG
VINPYNGDTAYNQKFKGRVTITRDTSASTAYMELSSLRSEDTAVYYCAR
DDGYYDYYFDVWGQGTTVTVSS Hu303_VH.1A
SEQ ID NO: 31
QVQLVQSGAEVKKPGASVKVSCKASGYTFTDYYMNWVRQAPGQRLEWMG
VINPYNGDTAYNQKFKGRVTITVDKSASTAYMELSSLRSEDTAVYYCTR
DDGYYDYYFDVWGQGTTVTVSS Hu303_VH.1B
SEQ ID NO: 32
QVQLVQSGAEVKKPGASVKVSCKASGYTLTDYYMNWVRQAPGQRLEWMG
VINPYNGDTAYNQKFKGRVTITVDKSASTAYMELSSLRSEDTAVYYCTR
DDGYYDYYFDVWGQGTTVTVSS Hu303_VH.1C
SEQ ID NO: 33
QVQLVQSGAEVKKPGASVKVSCKASGYTLTDYYMNWVRQAPGQRLEWIG
VINPYNGDTAYNQKFKGRATLTVDKSASTAYMELSSLRSEDTAVYYCTR
DDGYYDYYFDVWGQGTTVTVSS Hu303_VL.1 (identical to Hu303VL-CDR graft)
SEQ ID NO: 30
DIQMTQSPSSLSASVGDRVTITCRASQDIGSRLNWYQQKPGKAPKLLIY
ATSTLDSGVPSRFSGSGSGTDFTLTISSLQPEDFATYYCLQLASSPPTF
GGGTKVEIK Hu303_VL.1A
SEQ ID NO: 34
DIQMTQSPSSLSASVGDRVTITCRASQDIGSRLNWYQQKPGKAPKRLIY
ATSTLDSGVPSRFSGSRSGTDFTLTISSLQPEDFATYYCLQLASSPPTF
GGGTKVEIK Hu303_VL.1B
SEQ ID NO: 35
DIQMTQSPSSLSASVGDRVTITCRASQDIGSRLNWYQQKPGKAPKRLIY
ATSTLDSGVPKRFSGSRSGTDFTLTISSLQPEDFATYYCLQLASSPPTF
GGGTKVEIK Hu303_VL.1C
SEQ ID NO: 36
DIQMTQSPSSLSASVGDRVTITCRASQDIGSRLNWLQQKPGKAFKRLIY
ATSTLDSGVPKRFSGSRSGTDFTLTISSLQPEDFATYYCLQLASSPPTF
GGGTKVEIK Hu303_VL.1D
SEQ ID NO: 37
DIQMTQSPSSLSASVGDRVTLTCRASQDIGSRLNVVLQQKPGGAFKRLI
YATSTLDSGVPKRFSGSRSGTDFTLTISSLQPEDFADYYCLQLASSPPT
FGGGTKVEIK

Example 5. Preparation of Recombination and Humanized Antibody

The antibody was constructed with constant region derived from human heavy chain IgG4/light chain kappa in combination with each variable region, and a S228P mutation was made in Fc to increase the stability of the IgG4 antibody. The other mutations known in the art can also be used to increase its performance.

Constant region of heavy chain:
SEQ ID NO: 38
ASTKGPSVFPLAPCSRSTSESTAALGCLVKDYFPEPVTVSWNSGALTSG
VHTFPAVLQSSGLYSLSSVVTVPSSSLGTKTYTCNVDHKPSNTKVDKRV -continued
ESKYGPPCPPCPAPEFLGGPSVFLFPPKPKDTLMISRTPEVTCVVVDVS

QEDPEVQFNWYVDGVEVHNAKTKPREEQFNSTYRVVSVLTVLHQDWLNG

KEYKCKVSNKGLPSSIEKTISKAKGQPREPQVYTLPPSQEEMTKNQVSL

TCLVKGFYPSDIAVEWESNGQPENNYKTTPPVLDSDGSFFLYSRLTVDK

SRWQEGNVFSCSVMHEALHNHYTQKSLSLSLGK

Constant region of light chain:
SEQ ID NO: 39
RTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPV

TKSFNRGEC

1. Molecular Cloning of the Recombinant Antibody

The variable region coding sequences were obtained by sequencing the positive antibody molecules obtained from hybridoma screening. The primers were designed according to the obtained sequence, the sequencing gene was used as template, and various antibody VH/VK gene fragments were constructed by PCR, and then reconstituted with the expression vector pHr (with a signal peptide and hIgG4/hkappa constant region (CH1-FC/CL) fragment) to construct an expression plasmid VH-CH1-FC-pHr/VL-CL-pHr for full-length recombinant antibody.

2. Molecular Cloning of Humanized Antibody

The designed humanized antibody sequence was subjected to codon optimization and a coding sequence with human codon preference was generated. Primers were designed and various VH/VK gene fragments of the antibodies were constructed by PCR, and reconstituted with the expression vector pHr (with a signal peptide and hIgG4/hkappa constant region (CH1-FC/CL) fragment) to construct an expression plasmid VH-CH1-FC-pHr/VL-CL-pHr for full-length humanized antibody.

3. Expression and Purification of Recombination and Humanized Antibody

The plasmids for separate expression of antibody light chain and heavy chain were co-transfected into HEK293E cell at a ratio of 1:1.2. The expression supernatant was collected after 6 days and impurities were removed by high-speed centrifugation and then purified by Protein A column. The column was washed with PBS until the A280 reading was reduced to baseline. The target protein was eluted with acidic elution buffer, pH 3.0-pH 3.5, and neutralized with 1 M Tris-HCl, pH 8.0-9.0. The eluent was properly concentrated and further purified by gel chromatography Superdex200 (GE) which was equilibrated with PBS. The mismatch peak was excluded and the elution peak was collected. Then the correct sample was aliquoted and for use.

The performance and benefits of the antibody of the present invention are verified by biochemical test methods as below.

Test Example 1. ELISA Assay for the Binding of LAG-3 Antibody to Human LAG-3 Protein The binding ability of anti-LAG-3 antibody to human LAG-3 protein was detected by ELISA assay. LAG-3 fusion protein with Fc or mFc tag was immobilized into 96-well microtiter plate by binding to anti-Fc or mFc antibody coated in the microtiter plate, the strength of the signal after the addition of the antibody was used to determine the binding activity of the antibody to LAG-3, the specific experimental method is as follows.

The goat anti-human Fc antibody (Jackson Immuno Research, Cat No. 109-005-008) or goat anti-mouse Fc antibody (Sigma, Cat No. M3534-1ML) was diluted to a concentration of 2 µg/ml with PBS buffer at pH 7.4, and added to a 96-well plate at a volume of 50 µl/well and then, the plate was incubated in the incubator at 37° C. for 2 hours. After discarding the liquid, the plates were blocked with 200 µl/well of blocking solution containing 5% skim milk (Guangming skim milk) in PBS, and incubated in the incubator at 37° C. for 2.5 hours or overnight at 4° C. (16-18 hours). After blocking, the blocking solution was discarded and the plate was washed 5 times with PBST buffer (PH7.4 PBS containing 0.05% tweeen-20). LAG-3-Fc fusion protein (SEQ ID NO:3, produced in-house) or LAG-3-mFc fusion protein (SEQ ID NO: 4, produced in-house) was diluted with sample dilution (PH7.4 PBS containing 1% BSA) to 1 µg/ml and was added to each well, 50 µl/well. Then the plate was incubated in the incubator at 37° C. for 1 h or overnight at 4° C. After incubation, the reaction solution in the plate was discarded, and the plate was washed with PBST for 6 times, and then was added with 50 µl of various concentrations of the test antibody (hybridoma purified antibody or humanized antibody) diluted with sample dilution and the plate was incubated at 37° C. for 1 h. The plates was washed 5 times with PBST after incubation, and was added with 100 µl/well of goat anti-mouse (Jackson Immuno Research, Cat No. 115-035-003) or goat anti-human secondary antibody (Jackson Immuno Research, Cat No. 109-035-003) labeled with HRP, diluted in sample dilution, and the plate was incubated at 37° C. for 1 h. After washing the plates 6 times with PBST, 50 µl/well of TMB chromogenic substrate (KPL, Cat No. 52-00-03) was added to each well, and incubated at room temperature for 5-15 min, the reaction was stopped by the addition of 50 µl/well 1M H2SO4 to each well. The OD value at a wavelength of 450 nm was read on NOVOStar microplate reader, and then EC50 values of the binding of LAG-3 antibody to human LAG-3 were calculated. The results are shown in Table 8. The data showed that all the humanized antibodies obtained by the screening method in the present invention showed excellent binding activities to human LAG-3 protein.

TABLE 8

Determination of EC50 value for Candidate Antibody in Binding Assay

| Candidate Antibody | Binding ELISA EC50(nM) |
| --- | --- |
| mAb229 | 0.129 |
| Hu229-008 | 0.506 |
| Hu229-009 | 0.152 |
| Hu229-010 | 0.174 |
| Hu229-011 | 0.201 |
| Hu229-012 | 0.268 |
| Hu229-013 | 0.106 |
| Hu229-014 | 0.153 |
| Hu229-015 | 0.156 |
| Hu229-016 | 0.154 |
| Hu229-017 | 0.048 |
| Hu229-019 | 0.068 |
| mAb303 | 0.172 |
| Hu303-004 | 0.278 |
| Hu303-005 | 0.309 |
| Hu303-006 | 0.288 |
| Hu303-007 | 0.135 |
| Hu303-008 | 0.140 |
| Hu303-009 | 0.316 |
| Hu303-010 | 0.137 |

TABLE 8-continued

Determination of EC50 value for Candidate Antibody in Binding Assay

| Candidate Antibody | Binding ELISA EC50(nM) |
|---|---|
| Hu303-011 | 0.314 |
| Hu303-012 | 0.164 |
| Hu303-013 | 0.166 |
| Hu303-014 | 0.232 |
| Hu303-015 | 0.172 |
| Hu303-016 | 0.161 |
| Hu303-017 | 0.168 |
| Hu303-018 | 0.244 |
| Hu303-019 | 0.277 |
| Hu303-020 | 0.140 |
| Hu303-021 | 0.170 |
| Hu303-022 | 0.145 |
| Hu303-023 | 0.152 |

Test Example 2. Binding Assay of LAG-3 Antibody with Human LAG-3 Over-Expressing CHO-s Cells The binding ability of anti-LAG-3 antibody to LAG-3 protein over-expressing CHO-S cells was detected by binding assay. The full-length LAG-3 plasmid (produced in-house, SEQ ID NO: 2) was transfected into CHO-S cells by electroporation, and the expression level of LAG-3 was detected after two weeks of post-pressure screening. The LAG-3 over-expressing cells were fixed to the bottom of the 96-well plate, and the strength of the signal after the addition of the antibody was used to determine the binding activity of the antibody to human LAG-3 over-expressing CHO-s cells, the specific experimental method is as follows.

100 µl/well of cells were seeded into 96-well plate with a density of $4 \times 10^5$/ml and incubated overnight. The supernatant was discarded, and the plate was washed three times with PBS, added with 4% PFA, 100 µl/well, to fix for half an hour at room temperature, and then the plate was washed three times with PBS. After discarding the liquid, the plate was blocked with 200 µl/well of blocking solution containing 5% skim milk (Guangming skim milk) diluted in PBS, and incubated at 37° C. for 2.5 hours. After blocking, the blocking solution was discarded and the plate was washed 5 times with PBST buffer (PH7.4 PBS containing 0.05% tweeen-20), added with 50 µl/well of test antibody (Hybridoma purified antibody or humanized antibody) with different concentrations diluted with sample dilution, and then incubated in incubator at 37° C. for 1 h. The plate was washed 5 times with PBST after incubation, added with 100 µl/well of goat anti-mouse (Jackson Immuno Research, Cat No. 115-035-003) or goat anti-human secondary antibody (Jackson Immuno Research, Cat No. 109-035-003) labeled with HRP, diluted in sample dilution, and the plate was incubated at 37° C. for 1 h. After washing the plates 6 times with PBST, 50 µl of TMB chromogenic substrate (KPL, Cat No. 52-00-03) was added to each well, and incubated at room temperature for 5-15 min, the reaction was stopped by the addition of 50 µl 1M $H_2SO_4$ to each well. The OD value at a wavelength of 450 nm was read on NOVOStar microplate reader, and then the EC50 values of the binding of LAG-3 antibody to LAG-3 over-expressing CHOs cell were calculated.

Test Example 3. Assay for the Anti-LAG-3 Antibody in Blocking the Binding of LAG-3 Antigen to Daudi Cells Daudi cells (human leukemia cells, purchased from the Chinese Academy of Sciences cell bank) were seeded in 96-well plate with a density of $3 \times 10^5$/well. After centrifugation at 1000 rpm, the supernatant was discarded and then the plate was added with 4% PFA to fix for 30 minutes at room temperature. The plate was washed 4 times with PBS after discarding the fixed solution, and the plate was blocked with 200 µl/well of blocking solution containing 5% skim milk (Guangming skim milk) diluted in PBS, and incubated at 37° C. for 2.5 hours. After blocking, the blocking solution was discarded and the plate was washed 5 times with PBST buffer (PH7.4 PBS containing 0.05% tweeen-20), added with 50 µl/well mixture of biotin-labeled LAG-3-Fc fusion protein (produced in-house, SEQ ID NO: 3), diluted with dilution solution (PH7.4 PBS containing 1% BSA) at final concentration of 0.4 µg/ml, wherein the biotin (Biotin labeling kit, Dojindo Chemical, Cat No. LK03) was pre-mixed for an hour, and gradient concentrations of the antibody to be tested, then the plate was incubated at 37° C. for 1 h. The reaction solution was discarded and the plate was washed 5 times with PBST after incubation, added with 50 µl/well of HRP-labeled Streptavidin (Sigma, Cat No. 52438) which was diluted with sample dilution and the plate was incubated at 37° C. for 1 h. After washing the plate 5 times with PBST, 50 µl/well of TMB chromogenic substrate (KPL, Cat No. 52-00-03) was added to each well, and incubated at room temperature for 5-15 min, the reaction was stopped by the addition of 50 µl 1M $H_2SO_4$ to each well. The OD value at a wavelength of 450 nm was read on NOVOStar microplate reader, and then the activity of the LAG-3 antibody in blocking the binding of the antigen to Daudi cells was calculated. The results are shown in Table 9. The data show that all of the humanized antibodies obtained by the screening method in the present invention significantly blocked the binding of human LAG-3 antigen to Daudi cells.

TABLE 9

Determination of IC50 value of Candidate Antibody in Blocking Assay

| Candidate Antibody | Binding assay IC50 (nM) |
|---|---|
| mAb229 | 1.327 |
| Hu229-009 | 0.559 |
| Hu229-010 | 0.453 |
| Hu229-011 | 0.566 |
| Hu229-013 | 0.39 |
| Hu229-014 | 0.718 |
| Hu229-015 | 0.808 |
| Hu229-016 | 0.875 |
| Hu229-017 | 0.239 |
| Hu229-019 | 0.289 |
| mAb303 | 0.596 |
| Hu303-004 | 0.502 |
| Hu303-005 | 0.622 |
| Hu303-006 | 0.821 |
| Hu303-007 | 0.343 |
| Hu303-008 | 0.346 |
| Hu303-009 | 0.417 |
| Hu303-010 | 0.346 |
| Hu303-011 | 0.728 |
| Hu303-012 | 0.361 |
| Hu303-013 | 0.347 |
| Hu303-014 | 0.467 |
| Hu303-015 | 0.398 |
| Hu303-016 | 0.395 |
| Hu303-017 | 0.398 |
| Hu303-018 | 0.608 |
| Hu303-019 | 0.471 |
| Hu303-020 | 0.345 |
| Hu303-021 | 0.456 |
| Hu303-022 | 0.360 |
| Hu303-023 | 0.369 |

Test Example 4. BIAcore Assay for the Affinity of LAG-3 Antibody

1. The mouse anti-capture antibody was covalently linked to the CM5 biochip (Cat. #BR-1000-12, GE) according to the method described in the mouse anti-capture kit (Cat. #BR-1008-38, GE), so that the test antibody was captured via affinity. Then, the LAG-3-Flag antigen (produced in-house, SEQ ID NO:1) was flowed through the surface of the biochip, and the reaction signal was detected in real time by using a Biacore instrument to obtain the binding and dissociation curves, the value of affinity was obtained by fitting, see above table 2. After each cycle of dissociation is finished in the experiment, the biochip was washed and regenerated with a regeneration solution provided in the mouse anti-capture kit. The results demonstrate that the LAG-3 antibody mAb229 and mAb303 showed excellent binding activity and affinity to human LAG-3 protein.

2. The human anti-capture antibody was covalently linked to the CM5 biochip (Cat. #BR-1000-12, GE) according to the method described in the human anti-capture kit (Cat. #BR-1008-39, GE), so that the test antibody was captured via affinity. Then, the LAG-3-Flag antigen (produced in-house, SEQ ID NO:1) was flowed through the surface of the biochip, and the reaction signal was detected in real time using a Biacore instrument to obtain the binding and dissociation curves, the value of affinity was obtained by fitting, see table 10 below. After each cycle of dissociation is finished in the experiment, the biochip was washed and regenerated with a regeneration solution provided in the human anti-capture kit. The results demonstrate that the antibodies obtained by the screening method in present invention showed excellent binding activity and affinity to human LAG-3 protein.

TABLE 10

| Affinity of anti-LAG-3 Antibody | | |
| --- | --- | --- |
| Stationary phase | Mobile phase | Affinity(M) |
| mAb229 | LAG-3-Flag | 1.72E−11 |
| Hu229-009 | | 4.88E−11 |
| Hu229-010 | | 3.82E−11 |
| Hu229-013 | | 2.81E−11 |
| Hu229-014 | | 3.74E−11 |
| Hu229-015 | | 4.59E−11 |
| Hu229-017 | | 6.71E−11 |
| Hu229-019 | | 7.29E−11 |
| mAb303 | | 7.49E−11 |
| Hu303-004 | | 1.06E−09 |
| Hu303-005 | | 7.15E−11 |
| Hu303-006 | | 7.53E−11 |
| Hu303-009 | | 9.43E−10 |
| Hu303-010 | | 1.47E−10 |
| Hu303-014 | | 4.91E−10 |
| Hu303-016 | | 7.48E−11 |

Test Example 5. Activation of PBMC-T Lymphocytes

In order to study the effect of LAG-3 antibody on activating T lymphocytes, human peripheral blood mononuclear cells (PBMCs) were collected and purified. The secretion level of IL-2 cytokines was measured after stimulated with super-antigen of Staphylococcus aureus enterotoxin B (SEB) in vitro for 72 h. The experimental process is briefly described below:

Freshly isolated and purified PBMCs were seeded into 96-well cell culture plate with a cell density of about $1\times10^5$/well, and 100 ng/ml SEB super-antigen stimulus was added, and gradiently diluted antibody samples (diluted with medium) or medium as a blank control were added at the same time. Then, the plate was incubated at 37° C., 5% $CO_2$ for 72 h, the cell culture supernatant was collected. The level of the secreted IL-2 in the culture supernatant was measured by ELISA (BD, CAT #550611). Detailed procedures are indicated in the manufacturers' manual. The result was shown in FIG. 1. Both humanized LAG-3 antibodies Hu229-013 and Hu303-005 can enhance the levels of cytokine IL-2 secreted by the activated T lymphocytes to different degree, and has dose-depending effect of drug concentration.

Test Example 6. Inhibition of Subcutaneously Inoculated U-87MG Tumor by LAG-3 Antibody In this study, the effect of humanized anti LAG-3 antibody on the tumor volume of U-87 MG tumor bearing mice was measured.

100 µl of human glioma U87 MG cells ($3.5\times10^6$ cells) were inoculated subcutaneously in right ribs of NOD-SCID mice (Purchased from Changzhou Cavion Experimental Animal Co., Ltd.). When the tumor grew to 40 $mm^3$ after 10 to 14 days, the mice, excluding ones with too large or too small body weight or tumor volume, were randomly divided into three groups: a control group with Isotype matched hIgG, a group with LAG-3 candidate antibodies Hu229-013 and a group with LAG-3 candidate antibodies Hu303-005, according to the tumor volume (Grouping and dosage see Table 1), each group of 8 mice (DO). The PBMCs stimulated by CD3 antibody were injected into the tumor tissues at $5\times10^5$ cells/60 µl, and the injection of test antibody was started via i.p. injection, three times a week for total of 6 times.

Mice were measured for tumor volume twice a week, data were recorded. Tumor volume (V) was calculated as:

Tumor volume $(TV) = \frac{1}{2} \times a \times b^2$, wherein $a$ and $b$ represent length and width, respectively.

The tumor volume of each group was expressed as mean±standard error (Mean±SEM), and plotted with Graphpad Prism 5 software, analyzed with two way ANOVA statistical analysis, and the tumor inhibition rate was calculate according to the following formula:

Tumor proliferation rate $(T/C\%) = (T-T_0/C-C_0) \times 100\%$

Tumor inhibition rate % $TGI = 1 - T/C\%$

Figure 2:
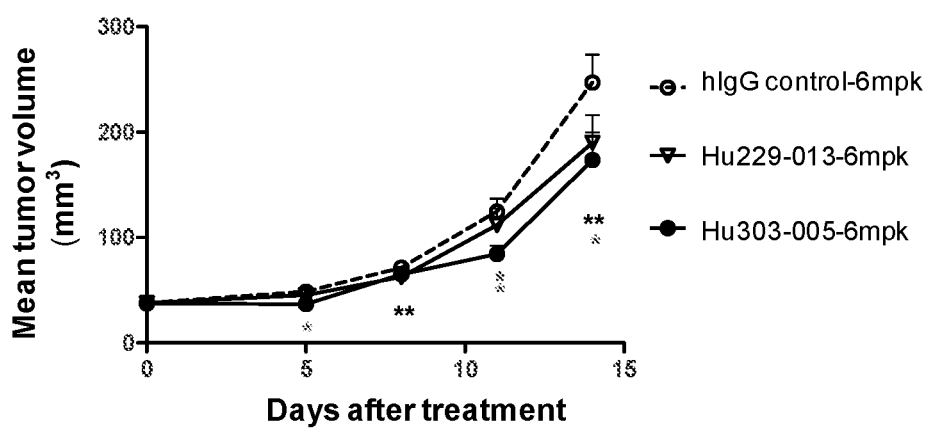
FIG. 2: Effect of humanized anti-LAG-3 antibody on tumor volume of U-87MG tumor-bearing mice. The results show that both LAG-3 antibody Hu229-013 6mpk and Hu303-005 6mpk have certain anti-tumor effects, and the tumor inhibition rates were 27.25% (p<0.05) and 34.94% (p<0.01), respectively, and there were significant differences compared to the control group (p<0.001 vs hIGg).

The result was shown in table 11 and FIG. 2, indicating that 14-day post administration, LAG-3 antibodies Hu229-013 6mpk and Hu303-005 6 mpk both have certain anti-tumor effect, and the tumor inhibition rates were 27.25% (p<0.05) and 34.94% (p<0.01), respectively. There was a significant difference compared to control group (p<0.001 vs hIGg).

TABLE 11

Effect of humanized anti-LAG-3 antibody on subcutaneously inoculated U-87MG Tumor in Mice.

| Groups | Dose(mpk) | Day 0 Mean ± SEM (mm³) | Day 14 Mean ± SEM(mm³) | P(vs hIgG) | % TGI at Day 14 |
|---|---|---|---|---|---|
| hIgG control | 6 | 37.9 ± 2.6 | 247.1 ± 26.5 | — | — |
| Hu229-013 | 6 | 37.9 ± 2.5 | 190.1 ± 26.2* | <0.05 | 27.25% |
| Hu303-005 | 6 | 37.7 ± 2.4 | 173.5 ± 26.5** | <0.01 | 34.94% |

D 0: First time of administration;
*p < 0.05,
**p < 0.01,
***p < 0.001 vs hIGg by two way ANOVA.

Test Example 7. Pharmacokinetics (PK) Assay of Humanized Anti-LAG-3 Antibodies Hu229-013 and Hu303-005 in Mouse Eighteen ICR mice, male, weighing from 18 to 22 g, were purchased from the West Poole-Bikai Experimental Animal Co., Ltd. During the feeding period, the mice were given ad libitum access to water and diet, the duration for adaption in the laboratory environment is not less than 3 days, with 12/12 hour light/dark cycle regulation, at the temperature of 16-26° C. and relative humidity of 40-70%. ICR mice were numbered and randomly divided into different groups one day before starting the experiment, each group of 3 mice. On the day of the experiment, two groups of mice were injected intravenously with humanized candidate antibody (Hu229-013) at dose of 3 mg/kg and 10 mg/kg, respectively; The other two groups of mice were injected intravenously with humanized candidate antibody (Hu303-005) at dose of 3 mg/kg and 10 mg/kg, respectively. The volume for intravenous injection is of 20 ml/kg.

The blood samples were collected at time point of 15 min, 8 h, 1 d, 2 d, 7 d, 10 d, 14 d, 21 d, 28 d, and 35 d post administration. Each time about 0.1 ml of whole blood was taken into the centrifuge tube without anticoagulant, placed at 4° C. for 30 min, and then centrifuged at 1000 g for 15 min. After that, the supernatant was pipetted into the EP tube and stored at −80° C.

The concentration of drug in serum was measured by ELISA, and the T1/2 and other main parameters were calculated by Winnolin software. The main pharmacokinetic parameters are shown in Table 12:

The AUCs of humanized LAG-3 antibodies Hu229-013 and Hu303-005 in mice were similar, and the AUCs and peak concentrations of these two antibodies at the dose of 3 and 10 mg/kg were linearly correlated with the increasing dose, and showed linear pharmacokinetic characteristic.

Test Example 8. Physical Stability of the Antibody

This test example was used to detect the physical stability of the humanized anti-LAG-3 antibodies Hu229-013 and Hu303-005.

The thermal stability of different antibodies was detected by DSC (Differential scanning calorimetry), and the stability of antibody in different buffer systems and different pH conditions was compared. The buffer systems corresponding to different pH values are, for example, PBS (pH7.4), 10 mM His/135 mM NaCl (pH6.0), 10 mM Acetate/135 mM NaCl (pH5.2).

The sample was dissolved in the corresponding buffer, and the concentration of the sample was controlled at about 1 mg/ml, and was detected using MicroCal* VP-Capillary DSC (Malvern). Prior to the test, each sample and blank buffer were degassed with vacuum degassing device for 1 to 2 min. 400 μl of sample or blank buffer was added to each well (the loading quantity was 300 μl). Finally, the two pairs of wells were added with 14% Decon 90 and ddH$_2$O, respectively, for washing. After the plate was loaded with sample, the plate was sealed with a plastic cover. Scanning was started from the temperature of 25° C. to 100° C. and the scanning rate is 60° C./h. The results are shown in table

TABLE 12

Pharmacokinetic parameters of Hu229-013 and Hu303-005 in mice

| | Hu229-013 | | Hu303-005 | |
|---|---|---|---|---|
| Dose(mg/kg) | 3 mg/kg | 10 mg/kg | 3 mg/kg | 10 mg/kg |
| $t_{max}$(hour) | 0.25 | 0.25 | 0.25 | 0.25 |
| $C_{max}$(ug/ml) | 51.6 ± 1.2 | 130 ± 20.2 | 68.2 ± 8.4 | 243. ± 19.9 |
| $AUC_{0-t}$ (ug/ml*h) | 5556 ± 891 | 17120 ± 4177 | 6386 ± 453 | 22609 ± 1567 |
| $AUC_{0-\infty}$ (ug/ml*h) | 5871 ± 1036 | 19736 ± 6142 | 7124 ± 581 | 27061 ± 5154 |
| $t_{1/2}$(h) | 183 ± 54 | 276 ± 193 | 232 ± 24 | 330 ± 194 |
| CLz/F(ml/min/kg) | 0.0087 ± 0.0015 | 0.0092 ± 0.0034 | 0.007 ± 0.0006 | 0.0063 ± 0.0011 |
| Vz/F(ml/kg) | 134 ± 16 | 186 ± 107 | 141 ± 14 | 168 ± 66 |
| $MRT_{0-\infty}$ (h) | 241 ± 59 | 353 ± 191 | 324 ± 37 | 411 ± 181 |

13, indicating that both antibodies Hu229-013 and Hu303-005 showed excellent thermal stability in several test systems.

TABLE 13

| Sample | Buffer | Tm-onset (° C.) | TM (° C.) |
|---|---|---|---|
| Hu229-013 | pH 7.4 | 61.67 | 71.68 |
| | pH 6.0 | 61.96 | 72.84 |
| | pH 5.2 | 67.3 | 73.14 |
| Hu303-005 | pH 7.4 | 61.85 | 70.19 |
| | pH 6.0 | 61.01 | 71.06 |
| | pH 5.2 | 60.84 | 70.45 |

The purity of the samples was monitored by SEC-HPLC, and the periodic stability under certain conditions was investigated. Exemplary conditions are, for example, controlling the concentration of the sample at about 50 mg/ml and comparing the stability of the different antibodies which were repeatedly frozen and thawed at −80° C. for 5 times in PBS (pH 7.4) system and stored at 4° C. and 40° C. for one month. The Xbridge protein BEH SEC 200A (Waters) HPLC column was used for detection. The results are shown in Table 14, indicating that both antibodies showed better stability.

TABLE 14

| | Hu229-013(Δ %) | Hu303-005(Δ %) |
|---|---|---|
| 4° C. | 0.2% | 0.2% |
| 40° C. | 2.2% | 2.7% |
| −80° C. frozen-thawed | 4% | 5% |

NOTE:
Δ % indicates that the rate of the reduced HPLC purity

Test Example 9. Chemical Stability of the Antibody

Deamidation is a common chemical modification of antibodies that may affect the stability at later stage, especially, it is generally desirable to avoid high degree of deamidation modification in amino acid residues at the CDR region or try to reduce the mutations. 500 μg of the test antibody was dissolved in 500 μl of PBS at pH 7.4, and then was placed in water-bath at 40° C. Samples were taken at day 0, 3, 7 for the enzymatic assay. 100 μg of each sample which was taken at different time points was dissolved in 100 μl of 0.2 M His-HCl, 8 M Gμa-HCl solution, pH 6.0, and 3 μl of 0.1 g/ml of DTT was added, and then the sample was placed in water-bath at 50° C. for 1 h. After ultrafiltration twice with 0.02 M His-HCl, pH 6.0, 3 μl of 0.25 mg/mL trypsin was added for enzymatic digestion in water-bath at 37° C. overnight. The deamidation modification was examined using LC-MS (Agilent 6530 Q-TOF), and the results are shown in Table 15.

TABLE 15

| Sample | Light/Heavy chain | Modification point | Day 0 | Day 7 |
|---|---|---|---|---|
| Hu229-013 | Light chain | N28 | 1.22% | 1.27% |
| | | N53 | 0.83% | 2.91% |
| Hu303-005 | Heavy chain | N55 | 2.86% | 3.55% |
| | Light chain | N34 | 2.1% | 1.93% |

NOTE:
N represents modified asparagine which was detected, the number represents the position counted from the N-terminus of the light chain or heavy chain. Percentage represents the ratio of the deamidation modification to the total peptide signal at this site detected by LC-MS.

The results of mass spectrometry show that there was no obvious high proportion of deamidation modification sites in the detected antibodies, suggesting that chemical stability of the antibody is good at later stage.

The invention claimed is:

1. An anti-LAG-3 antibody or the antigen-binding fragment thereof, comprising a heavy chain variable region (VH) comprising complementarity determining regions HCDR1, HCDR2, and HCDR3, and a light chain variable region (VL) comprising complementarity determining regions LCDR1, LCDR2, and LCDR3,
wherein the
HCDR1, HCDR2, and HCDR3 comprises SEQ ID NO: 12, SEQ ID NO: 13 and SEQ ID NO: 14 respectively; and wherein the LCDR1, LCDR2, and LCDR3 comprises SEQ ID NO: 18, SEQ ID NO: 19 and SEQ ID NO: 20 respectively.

2. The anti-LAG-3 antibody or the antigen-binding fragment thereof of claim 1, wherein the antibody or the antigen-binding fragment thereof is a murine antibody or the antigen-binding fragment thereof.

3. The anti-LAG-3 antibody or the antigen-binding fragment thereof of claim 2, wherein the murine antibody or the antigen-binding fragment thereof comprises a heavy chain variable region comprising a sequence as set forth in SEQ ID NO: 7 and a light chain variable region comprising a sequence as set forth in SEQ ID NO: 8.

4. The anti-LAG-3 antibody or the antigen-binding fragment thereof of claim 1, wherein the light chain variable region comprises a light chain FR region derived from a murine κ chain or a variant thereof, or a light chain FR region derived from a murine λ chain or a variant thereof.

5. The anti-LAG-3 antibody or the antigen-binding fragment thereof of claim 1, wherein the antibody light chain comprises a light chain constant region derived from a murine κ chain or a variant thereof, or a light chain constant region derived from a murine λ chain or a variant thereof; wherein the antibody heavy chain comprises a heavy chain constant region derived from a murine IgG1 or a variant thereof, a heavy chain constant region derived from a murine IgG2 or a variant thereof, or a heavy chain constant region derived from a murine IgG3 or a variant thereof.

6. The anti-LAG-3 antibody or the antigen-binding fragment thereof of claim 1, wherein the antibody or the antigen-binding fragment thereof is a chimeric antibody or the antigen-binding fragment thereof or a humanized antibody or the antigen-binding fragment thereof.

7. The anti-LAG-3 antibody or the antigen-binding fragment thereof of claim 6, wherein the heavy chain variable region comprises a heavy chain FR sequence that is derived from a combination sequence of human germline heavy chain IGHV1-3*01 and hjh6.1, or a mutant sequence thereof.

8. The anti-LAG-3 antibody or the antigen-binding fragment thereof of claim 7, wherein the heavy chain variable region comprises a sequence that is at least 85% identical to SEQ ID NO: 29.

9. The anti-LAG-3 antibody or antigen-binding fragment thereof of claim 7, wherein the heavy chain FR sequence comprises one or more amino acid back-mutations, wherein the one or more amino acid back-mutations are selected from the group consisting of F29L, A97T, M48I1, V68A, I70L, R72V and T74K.

10. The anti-LAG-3 antibody or the antigen-binding fragment thereof of claim 7, wherein the heavy chain variable region comprises a sequence that is at least 85% identical to SEQ ID NO:29, SEQ ID NO:31, SEQ ID NO:32 or SEQ ID NO: 33.

11. The anti-LAG-3 antibody or the antigen-binding fragment thereof of claim 6, wherein the light chain variable region comprises a light chain FR sequence that is derived from a combination sequence of human germline light chain IGKV1-39*01 and hjk4.1, or a mutant sequence thereof.

12. The anti-LAG-3 antibody or the antigen-binding fragment thereof of claim 11, wherein the light chain variable region sequence comprises a sequence that is at least 85% identical to.

13. The anti-LAG-3 antibody or the antigen-binding fragment thereof of claim 11, wherein the light chain FR sequence comprises one or more amino acid back-mutations, wherein the one or more back-mutations are selected from the group consisting of L46R, G66R, S60K, P44F, Y36L, K42G, I21L and T85D.

14. The anti-LAG-3 antibody or the antigen-binding fragment thereof of claim 11, wherein the light chain variable region comprises a sequence that is at least 85% identical to SEQ ID NO: 30, SEQ ID NO: 34, SEQ ID NO: 35, SEQ ID NO: 36, or SEQ ID NO: 37.

15. The anti-LAG-3 antibody or the antigen-binding fragment thereof of claim 6, wherein the humanized antibody or the antigen-binding fragment thereof comprises:
a heavy chain variable region, wherein the heavy chain variable region sequence comprises a sequence that is at least 85% identical to SEQ ID NO: 29, SEQ ID NO: 31, SEQ ID NO: 32 or SEQ ID NO: 33; and a light chain variable region, wherein the light chain variable region comprises a sequence that is at least 85% identical to SEQ ID NO: 30, SEQ ID NO: 34, SEQ ID NO: 35, SEQ ID NO: 36 or SEQ ID NO: 37.

16. The anti-LAG-3 antibody or the antigen-binding fragment thereof of claim 6, wherein the antibody or the antigen-binding fragment thereof comprises a combination of a heavy chain variable region and a light chain variable region selected from the group consisting of:
1) the heavy chain variable region of SEQ ID NO: 29 and the light chain variable region of SEQ ID NO: 30;
2) the heavy chain variable region of SEQ ID NO: 29 and the light chain variable region of SEQ ID NO: 34;
3) the heavy chain variable region of SEQ ID NO: 29 and the light chain variable region of SEQ ID NO: 35;
4) the heavy chain variable region of SEQ ID NO: 29 and the light chain variable region of SEQ ID NO: 36;
5) the heavy chain variable region of SEQ ID NO: 29 and the light chain variable region of SEQ ID NO: 37;
6) the heavy chain variable region of SEQ ID NO: 31 and the light chain variable region of SEQ ID NO: 30;
7) the heavy chain variable region of SEQ ID NO: 31 and the light chain variable region of SEQ ID NO: 34;
8) the heavy chain variable region of SEQ ID NO: 31 and the light chain variable region of SEQ ID NO: 35;
9) the heavy chain variable region of SEQ ID NO: 31 and the light chain variable region of SEQ ID NO: 36;
10) the heavy chain variable region of SEQ ID NO: 31 and the light chain variable region of SEQ ID NO: 37;
11) the heavy chain variable region of SEQ ID NO: 32 and the light chain variable region of SEQ ID NO: 30;
12) the heavy chain variable region of SEQ ID NO: 32 and the light chain variable region of SEQ ID NO: 34;
13) the heavy chain variable region of SEQ ID NO: 32 and the light chain variable region of SEQ ID NO: 35;
14) the heavy chain variable region of SEQ ID NO: 32 and the light chain variable region of SEQ ID NO: 36;
15) the heavy chain variable region of SEQ ID NO: 32 and the light chain variable region of SEQ ID NO: 37;
16) the heavy chain variable region of SEQ ID NO: 33 and the light chain variable region of SEQ ID NO: 30;
17) the heavy chain variable region of SEQ ID NO: 33 and the light chain variable region of SEQ ID NO: 34;
18) the heavy chain variable region of SEQ ID NO: 33 and the light chain variable region of SEQ ID NO: 35;
19) the heavy chain variable region of SEQ ID NO: 33 and the light chain variable region of SEQ ID NO: 36; and
20) the heavy chain variable region of SEQ ID NO: 33 and the light chain variable region of SEQ ID NO: 37.

17. The anti-LAG-3 antibody or the antigen-binding fragment thereof of claim 16, wherein the antibody or the antigen-binding fragment thereof comprises a heavy chain variable region of SEQ ID NO: 29 and a light chain variable region of SEQ ID NO: 34.

18. The anti-LAG-3 antibody or the antigen-binding fragment thereof of claim 6, wherein the heavy chain comprises a heavy chain constant region derived from a human IgG1 heavy chain constant region or a variant thereof, a human IgG2 heavy chain constant region or a variant thereof, a human IgG3 heavy chain constant region or a variant thereof, or a human IgG4 heavy chain constant region or a variant thereof;

wherein the light chain comprises a light chain constant region derived from a human κ chain or a variant thereof, or a human λ chain or a variant thereof.

19. The anti-LAG-3 antibody or the antigen-binding fragment thereof of claim 18, wherein the heavy chain constant region comprises SEQ ID NO: 38; and wherein the light chain constant region comprises SEQ ID NO: 39.

20. An anti-LAG-3 antibody or the antigen-binding fragment thereof, wherein the HCDR1, HCDR2, and HCDR3 are identical to complementarity determining regions of SEQ ID NO: 7 and the LCDR1, LCDR2, and LCDR3 are identical to complementarity determining regions of SEQ ID NO: 8.

21. The anti-LAG-3 antibody or the antigen-binding fragment thereof of claim 20, wherein the complementarity determining regions are defined by Kabat numbering.

* * * * *

UNITED STATES PATENT AND TRADEMARK OFFICE
CERTIFICATE OF CORRECTION

| | |
|---|---|
| PATENT NO. | : 11,155,617 B2 |
| APPLICATION NO. | : 16/312174 |
| DATED | : October 26, 2021 |
| INVENTOR(S) | : Zhuoxiao Cao et al. |

It is certified that error appears in the above-identified patent and that said Letters Patent is hereby corrected as shown below:

In the Claims

Claim 12: In Column 72, Line 51, please delete "identical to" and insert -- identical to SEQ ID NO: 30 --.

Signed and Sealed this
Second Day of May, 2023

*Katherine Kelly Vidal*

Katherine Kelly Vidal
*Director of the United States Patent and Trademark Office*